(12) United States Patent
Ray et al.

(10) Patent No.: US 11,186,560 B2
(45) Date of Patent: Nov. 30, 2021

(54) ARTHROPOD REPELLENT CHEMICALS

(71) Applicant: The Regents of the University of California, Oakland, CA (US)

(72) Inventors: Anandasankar Ray, Riverside, CA (US); Christine Krause Pham, La Crescenta, CA (US); Sean Michael Boyle, Sunnyvale, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/289,239

(22) Filed: Feb. 28, 2019

(65) Prior Publication Data

US 2019/0194158 A1 Jun. 27, 2019

Related U.S. Application Data

(63) Continuation of application No. 15/694,439, filed on Sep. 1, 2017, now abandoned, which is a continuation of application No. 15/073,698, filed on Mar. 18, 2016, now abandoned.

(60) Provisional application No. 62/134,882, filed on Mar. 18, 2015.

(51) Int. Cl.

| | | |
|---|---|---|
| *A01N 43/08* | (2006.01) | |
| *A01N 43/78* | (2006.01) | |
| *A01N 43/28* | (2006.01) | |
| *A01N 43/36* | (2006.01) | |
| *A01N 43/42* | (2006.01) | |
| *A01N 43/26* | (2006.01) | |
| *A01N 43/20* | (2006.01) | |
| *A01N 43/16* | (2006.01) | |
| *A01N 31/04* | (2006.01) | |
| *A01N 35/06* | (2006.01) | |
| *A01N 27/00* | (2006.01) | |
| *C07D 335/02* | (2006.01) | |
| *C07D 207/26* | (2006.01) | |
| *C07D 207/16* | (2006.01) | |
| *C07D 317/20* | (2006.01) | |
| *A01N 43/32* | (2006.01) | |
| *C07D 319/06* | (2006.01) | |
| *C07C 13/20* | (2006.01) | |
| *C07D 277/04* | (2006.01) | |
| *C07D 215/06* | (2006.01) | |
| *C07C 13/23* | (2006.01) | |

(52) U.S. Cl.
CPC .......... *C07D 335/02* (2013.01); *A01N 27/00* (2013.01); *A01N 31/04* (2013.01); *A01N 35/06* (2013.01); *A01N 43/08* (2013.01); *A01N 43/16* (2013.01); *A01N 43/20* (2013.01); *A01N 43/26* (2013.01); *A01N 43/28* (2013.01); *A01N 43/32* (2013.01); *A01N 43/36* (2013.01); *A01N 43/42* (2013.01); *A01N 43/78* (2013.01); *C07C 13/20* (2013.01); *C07C 13/23* (2013.01); *C07D 207/16* (2013.01); *C07D 207/26* (2013.01); *C07D 215/06* (2013.01); *C07D 277/04* (2013.01); *C07D 317/20* (2013.01); *C07D 319/06* (2013.01); *C07C 2601/16* (2017.05)

(58) Field of Classification Search
CPC ...... C07D 335/02; A01N 43/08; A01N 43/16; A01N 43/60; A01N 31/04; A01N 35/06
See application file for complete search history.

(56) References Cited

U.S. PATENT DOCUMENTS

| | | | |
|---|---|---|---|
| 3,668,226 A | 6/1972 | Quintana et al. | |
| 4,447,447 A | 5/1984 | Hreschak et al. | |
| 4,466,967 A * | 8/1984 | Smolanoff | A01N 47/38 |
| | | | 514/307 |
| 4,469,613 A | 9/1984 | Munteanu et al. | |
| 4,496,467 A | 1/1985 | Munteanu et al. | |
| 4,548,764 A | 10/1985 | Munteanu et al. | |
| 5,089,469 A | 2/1992 | Zampino et al. | |
| 5,175,175 A | 12/1992 | Wilson et al. | |

(Continued)

FOREIGN PATENT DOCUMENTS

| | | |
|---|---|---|
| CN | 1809368 A | 7/2006 |
| CN | 101268786 A | 9/2008 |

(Continued)

OTHER PUBLICATIONS

Skinner et al., "Topical Mosquito Repellents IX: Quinolines, Isoquinolines, and Quinoxalines", Journal of Pharmaceutical Sciences, vol. 65, No. 9. Sep. 1976, pp. 1404-1407.*

(Continued)

*Primary Examiner* — Yong L Chu
(74) *Attorney, Agent, or Firm* — Morrison & Foerster LLP

(57) ABSTRACT

Compositions and methods for repelling arthropods. The compositions include a carrier and an arthropod repelling compound, which can be a compound discovered by a novel and complex cheminformatic process to demonstrate repellency behavior across a broad spectrum of arthropods. The compound can be a thiane compound, a pyrrolidone compound, a cyclohexadiene compound, a cyclohexenone compound, a cyclohexene compound, a furanone compound, a pyran compound, a tetrahydropyran compound, a thiazolidine compound, a thiazoline compound, a dihydrothiophene compound, a dithiolane compound, a dithiane compound, an epoxide compound, an oxathiane compound, a cyclopentene compound, a cyclohexane compound, a quinoline compound, an oxazoline compound, a tetrahydropyridine compound, and an imidazolidinone compound, or a combination thereof.

16 Claims, 19 Drawing Sheets

(56) References Cited

U.S. PATENT DOCUMENTS

| | | |
|---|---|---|
| 5,227,163 A | 7/1993 | Eini et al. |
| 5,354,783 A | 10/1994 | Marin et al. |
| 5,653,991 A | 8/1997 | Rod |
| 5,698,209 A | 12/1997 | Shono et al. |
| 6,083,498 A | 7/2000 | Landolt |
| 6,106,821 A | 8/2000 | Baker et al. |
| 6,187,926 B1 * | 2/2001 | Osawa ............... C07D 215/233 546/153 |
| 6,192,621 B1 | 2/2001 | Fain |
| 6,267,953 B1 | 7/2001 | Bernier et al. |
| 6,372,804 B1 | 4/2002 | Ikemoto et al. |
| 6,562,841 B1 | 5/2003 | Klun et al. |
| 6,719,959 B1 | 4/2004 | Gonzalez et al. |
| 6,800,279 B2 | 10/2004 | Bernier et al. |
| 6,958,146 B2 | 10/2005 | Askham et al. |
| 7,867,479 B2 | 1/2011 | Dunham et al. |
| 8,048,683 B2 | 11/2011 | Grau et al. |
| 8,092,790 B2 | 1/2012 | Dunham et al. |
| 8,658,223 B2 | 2/2014 | Willis et al. |
| 8,685,964 B2 | 4/2014 | Bretschneider et al. |
| 8,945,595 B2 | 2/2015 | Ray et al. |
| 9,307,763 B2 | 4/2016 | Ray et al. |
| 9,491,942 B2 | 11/2016 | Ray et al. |
| 9,897,592 B2 | 2/2018 | Ray et al. |
| 9,910,044 B2 | 3/2018 | Ray et al. |
| 10,292,396 B2 | 5/2019 | Ray et al. |
| 10,768,168 B2 | 9/2020 | Ray et al. |
| 2002/0028191 A1 | 3/2002 | Bernier et al. |
| 2004/0223998 A1 | 11/2004 | Iyer et al. |
| 2004/0242699 A1 | 12/2004 | Askham et al. |
| 2005/0008714 A1 | 1/2005 | Enan |
| 2006/0189690 A1 | 8/2006 | Dunham et al. |
| 2006/0193881 A1 | 8/2006 | Bedoukian |
| 2007/0142795 A1 | 6/2007 | Cohen et al. |
| 2007/0157323 A1 | 7/2007 | Carlson et al. |
| 2007/0264297 A1 | 11/2007 | Scialdone et al. |
| 2009/0047379 A1 | 2/2009 | Dewis et al. |
| 2009/0148398 A1 | 6/2009 | Vander et al. |
| 2009/0176229 A1 | 7/2009 | Tracey et al. |
| 2009/0196838 A1 | 8/2009 | Gupta et al. |
| 2010/0009002 A1 | 1/2010 | Simonetta |
| 2010/0021392 A1 | 1/2010 | Kritikou |
| 2010/0074972 A1 | 3/2010 | Rouseff et al. |
| 2010/0144888 A1 | 6/2010 | Bessette |
| 2010/0247684 A1 | 9/2010 | Reid et al. |
| 2011/0166164 A1 | 7/2011 | Brewster et al. |
| 2011/0244056 A1 | 10/2011 | Santra |
| 2011/0263585 A1 | 10/2011 | Bernasconi et al. |
| 2012/0015841 A1 | 1/2012 | Shekdar et al. |
| 2012/0045525 A1 | 2/2012 | Ma |
| 2013/0041046 A1 * | 2/2013 | Tachdjian ............ C07D 451/06 514/788 |
| 2013/0101687 A1 | 4/2013 | Wills et al. |
| 2013/0236417 A1 | 9/2013 | Ray et al. |
| 2014/0013654 A1 * | 1/2014 | Burke .................... A01N 25/04 43/132.1 |
| 2014/0303114 A1 | 10/2014 | Mesina |
| 2015/0126437 A1 | 5/2015 | Ray et al. |
| 2015/0223458 A1 | 8/2015 | Ray et al. |
| 2015/0377897 A1 | 12/2015 | Ray et al. |
| 2016/0003805 A1 | 1/2016 | Ray et al. |
| 2016/0272612 A1 | 9/2016 | Ray et al. |
| 2017/0079274 A1 | 3/2017 | Ray et al. |
| 2017/0292944 A1 | 10/2017 | Ray et al. |
| 2017/0369468 A1 | 12/2017 | Ray et al. |
| 2018/0055032 A1 | 3/2018 | Ray et al. |
| 2018/0188235 A1 | 7/2018 | Ray et al. |

FOREIGN PATENT DOCUMENTS

| | | | |
|---|---|---|---|
| EP | 552405 B1 | 7/1993 | |
| EP | 1131044 A1 | 9/2001 | |
| FR | 2777014 A1 | 10/1999 | |
| JP | 7-29889 B2 | 4/1995 | |
| JP | 2000-290104 A | 10/2000 | |
| JP | 2001-278708 A | 10/2001 | |
| KR | 2010-0121237 | * 10/2010 | ............... A61K 8/49 |
| WO | 1998/023150 A1 | 6/1998 | |
| WO | 2000/027197 A1 | 5/2000 | |
| WO | 2000/065910 A1 | 11/2000 | |
| WO | 2002/000021 A2 | 1/2002 | |
| WO | 2005/020947 A1 | 3/2005 | |
| WO | 2007/056043 A2 | 5/2007 | |
| WO | 2008/110984 A1 | 9/2008 | |
| WO | 2010/027783 A1 | 3/2010 | |
| WO | 2010/102049 A2 | 9/2010 | |
| WO | 2010/143752 A2 | 12/2010 | |
| WO | 2011/040252 A1 | 4/2011 | |
| WO | WO-2010101462 A3 | 11/2011 | |
| WO | 2012/018153 A1 | 2/2012 | |
| WO | 2012/091156 A1 | 7/2012 | |
| WO | 2013/010099 A1 | 1/2013 | |
| WO | 2013/050902 A1 | 4/2013 | |
| WO | 2013/059364 A2 | 4/2013 | |
| WO | 2013/165477 A1 | 11/2013 | |
| WO | 2014/028835 A2 | 2/2014 | |
| WO | 2014/144685 A2 | 9/2014 | |

OTHER PUBLICATIONS

Abramson et al., "Proboscis Conditioning Experiments with Honeybees, *Apis mellifera Caucasica*, with Butyric Acid and DEET Mixture as Conditioned and Unconditioned Stimuli", Journal of Insect Science, vol. 10, No. 122, 2010, pp. 1-17.

Abuin et al., "Functional Architecture of Olfactory Ionotropic Glutamate Receptors", Neuron, vol. 69, No. 1, Jan. 13, 2011, pp. 44-60.

Al et al., "Acid Sensing by the *Drosophila* Olfactory System", Nature, vol. 468, No. 7324, Dec. 2, 2010, pp. 691-695.

"Allantoin", Pubchem, retrieved from <https://pubchem.ncbi.nlm.nih.gov/compound/allantoin#section=Top>, Last Visited on Mar. 14, 2018, pp. 1-58.

Andreev et al., "New Insect Repellents for Protection of Humans and Animals from Bloodsucking Flies, Mosquitoes, Midges, and Gnats", Chemical Abstracts Service, Columbus, Ohio, US, 1958, XP-002744302, Database Accession No. 1960:64502, 2 pages.

Baccino et al., "Sharing an Olfactory Experience: The Impact of Oral Communication", Food Quality and Preference, vol. 21. No. 5, 2010, pp. 443-452.

Bar-Zeev et al., "The Response of the Adults of the Khapra Beetle *Trogoderma granarium* Everts (Coleoptera, Dermestidae) to Various Synthetic Compounds", Rivista Di Parassitologia, vol. XL, No. 1/2, 1979, pp. 49-55.

Bell et al., "Behavior Reveals Selective Summation and Max Pooling among Olfactory Processing Channels", Neuron, vol. 91, Jul. 20, 2016, pp. 425-438.

Bellmann et al., "Optogenetically Induced Olfactory Stimulation in *Drosophila* Larvae Reveals the Neuronal Basis of Odor-Aversion behaviour", Frontiers in Behavioral Neuroscience, vol. 4, No. 27, Jun. 2010, pp. 1-10.

Benton et al., "Variant Ionotropic Glutamate Receptors as Chemosensory Receptors in *Drosophila*", Cell, vol. 136, Jan. 9, 2009, pp. 149-162.

Bernier et al., "Analysis of Human Skin Emanations by Gas Chromatography/Mass Spectrometry. 1. Thermal Desorption of Attractants for the Yellow Fever Mosquito (*Aedes aegypti*) from Handled Glass Beads", Analytical Chemistry, vol. 71, No. 1, Jan. 1, 1999, pp. 1-7.

Bernier et al., "Analysis of Human Skin Emanations by Gas Chromatography/Mass Spectrometry. 2. Identification of Volatile Compounds that are Candidate Attractants for the Yellow Fever Mosquito (*Aedes Aegypti*)", Analytical Chemistry, vol. 72, No. 4, Feb. 15, 2000, pp. 747-756.

Boeckh et al., "Acylated 1,3-Aminopropanols as Repellents against Bloodsucking Arthropods", Pesticide Science, vol. 48, 1996, pp. 359-373.

Bohbot et al., "Selectivity of Odorant Receptors in Insects", Frontiers in Cellular Neuroscience, vol. 6, No. 29, 2012, pp. 1-4.

(56) References Cited

OTHER PUBLICATIONS

Braks et al., "Infochemicals in Mosquito Host Selection: Human Skin Microflora and Plasmodium Parasites", Parasitology Today, vol. 15, No. 10, 1999, pp. 409-413.
Bruyne et al., "Odor Coding in a Model Olfactory Organ: The Drosophila Maxillary Palp", The Journal of Neuroscience, vol. 19, No. 11, 1999, pp. 4520-4532.
Burton, D. J., "Intrinsic Mosquito Repellency Values of Some Chemical Compounds", American Perfumer and Cosmetics, vol. 84, Apr. 1969, pp. 41-44.
Butler, Declan, "Mosquitoes Score in Chemical War", Nature, vol. 475, No. 19, Jul. 7, 2011, 1 page.
Cardé et al., "Host Finding by Female Mosquitoes: Mechanisms of Orientation to Host Odours and Other Cues", Olfaction in Vector-Host Interactions, 2010, pp. 115-141.
Cardé et al., "Navigational Strategies Used by Insects to Find Distant, Wind-Borne Sources of Odor", J Chem Ecol, vol. 34, 2008, pp. 854-866.
Carey et al., "Odorant Reception in the Malaria Mosquito Anopheles gambiae", Nature, 2010, pp. 1-7.
Chang et al., "LIBSVM: A Library for Support Vector Machines", This LIBSVM implementation document was created in 2001 and has been maintained at <http://www.csie.ntu.edu.tw/~cjlin/papers/libsvm.pdf>, 2001, pp. 1-39.
"Chemical Products Catalog (Shanghai)", Scientific and Technical Information Research Institute of Bureau of Chemical Industry, Shanghai, Feb. 29, 1992, pp. 177, 180, 450 (See Communication under 37 CFR § 1.98(a) (3)).
Chiang et al., "Three-Dimensional Reconstruction of Brain-Wide Wiring Networks in Drosophila at Single-Cell Resolution", Current Biology, vol. 21, Jan. 11, 2011, pp. 1-11.
Cook et al., "The Use of Push-Pull Strategies in Integrated Pest Management", Annual Review of Entomology, vol. 52, 2007, pp. 375-400.
Cooperband et al., "Orientation of Culex Mosquitoes to Carbon Dioxidebaited Traps: Flight Manoeuvres and Trapping Efficiency", Medical and Veterinary Entomology, vol. 20, 2006, pp. 11-26.
Cork et al., "Identification of Electrophysiologically-Active Compounds for the Malaria Mosquito, Anopheles gambiae, in Human Sweat Extracts", Medical and Veterinary Entomology, vol. 10, 1996, pp. 269-276.
Cortes et al., "Support-Vector Networks", Machine Learning, vol. 20, 1995, pp. 273-297.
Croset et al., "Ancient Protostome Origin of Chemosensory Ionotropic Glutamate Receptors and the Evolution of Insect Taste and Olfaction", Plos Genetics, vol. 6, No. 8, Aug. 2010, pp. 1-20.
Curran et al., "Comparison of the Volatile Organic Compounds Present in Human Odor Using SPME-GC/MS", Journal of Chemical Ecology, vol. 31, No. 7, Jul. 2005, pp. 1607-1619.
Dekker et al., "Carbon Dioxide Instantly Sensitizes Female Yellow Fever Mosquitoes to Human Skin Odours", The Journal of Experimental Biology, vol. 208, 2005, pp. 2963-2972.
Dekker et al., "Identification of Mosquito Repellent Odours from Ocimum Forskolei", Parasites & Vectors, vol. 4, No. 183, 2011, pp. 1-7.
Dekker et al., "Moment-to-Moment Flight Manoeuvres of the Female Yellow Fever Mosquito (Aedes aegypti L.) in Response to Plumes of Carbon Dioxide and Human Skin Odour", The Journal of Experimental Biology, vol. 214, 2011, pp. 3480-3494.
Dekker et al., "Structure of Host-Odour Plumes Influences Catch of Anopheles Gambiae S.S. and Aedes Aegypti in a Dualchoice Olfactometer", Physiological Entomology, vol. 26, 2001, pp. 124-134.
Douglas et al., "Chemical Odorant of Colonial Seabird Repels Mosquitoes", Journal of Medical Entomology, vol. 42, No. 4, Jul. 2005, pp. 647-651.
Enjin et al., "Humidity Sensing in Drosophila", Current Biology, vol. 26, May 23, 2016, pp. 1-7.

Erdelyan et al., "Functional Validation of the Carbon Dioxide Receptor Genes in Aedes aegypti Mosquitoes using RNA Interference", Insect Molecular Biology, vol. 21, No. 1, 2012, pp. 119-127.
"Ethylhexanoate—Identification, Toxicity, Use, Water Pollution Potential, Ecological Toxicity and Regulatory Information", PAN Pesticides Database—Chemicals, May 11, 2005, pp. 1-5.
Final Office Action received for U.S. Appl. No. 12/398,164, dated Apr. 16, 2014, 17 pages.
Final Office Action received for U.S. Appl. No. 12/398,164, dated Apr. 20, 2012, 10 pages.
Final Office Action received for U.S. Appl. No. 14/351,642, dated Feb. 9, 2017, 12 pages.
Final Office Action received for U.S. Appl. No. 15/279,278, dated Mar. 19, 2018, 10 pages.
Fischler et al., "The Detection of Carbonation by the Drosophila Gustatory System", Nature, vol. 448, Aug. 30, 2007, pp. 1054-1057.
Gallagher et al., "Analyses of Volatile Organic Compounds from Human Skin", Br J Dermatol, vol. 159, No. 4, Sep. 2008, pp. 780-791.
Gaudin et al., "Carboxamides Combining Favorable Olfactory Properties with Insect Repellency", Chemistry & Biodiversity, vol. 5, 2008, pp. 617-635.
Ghaninia et al., "Natural Odor Ligands for Olfactory Receptor Neurons of the Female Mosquito Aedes aegypti: Use of Gas Chromatography-linked Single Sensillum Recordings", The Journal of Experimental Biology, vol. 211, 2008, pp. 3020-3027.
Gillies, M. T.., "The Role of Carbon Dioxide in Host-Finding by Mosquitoes (Diptera culicidae): A Review", Bull. Ent. Res., vol. 70, 1980, pp. 525-532.
Godavarthy et al., "Improved Structure-Property Relationship Models for Prediction of Critical Properties", Fluid Phase Equilibria, vol. 264, 2008, pp. 122-136.
Grant et al., "Olfaction in Mosquito-Host Interactions", Ciba Foundation Symposium 200, 1996, 10 pages.
Gupta et al., "Discovery and Design of New Arthropod/Insect Repellents by Computer-Aided Molecular Modeling", Insect Repellents Principles, Methods, and Uses, 2007, pp. 195-228.
Gutierrez-Osuna, Ricardo, "Pattern Analysis for Machine Olfaction: A Review", IEEE Sensors Journal, vol. 2, No. 3, Jun. 2002, pp. 189-202.
Haasen et al., "Pharmacological Profiling of Chemokine Receptor-Directed Compounds Using High-Content Screening", Journal of Biomolecular Screening, vol. 13, No. 1, 2008, pp. 40-53.
Haddad et al., "A Metric for Odorant Comparison", Nature Methods, 2008, pp. 1-5.
Halbert et al., "Plant-Derived Compounds and Extracts with Potential as Aphid Repellents", Annals of Applied Biology, vol. 154, 2009, pp. 303-307.
Hallem et al., "Coding of Odors by a Receptor Repertoire", Cell, vol. 125, Apr. 7, 2006, pp. 143-160.
Hawkins et al., "Conformer Generation with OMEGA: Algorithm and Validation Using High Quality Structures from the Protein Databank and Cambridge Structural Database", J. Chem. Inf. Model, vol. 50, 2010, pp. 572-584.
Hayes et al., "Identification of a Host Compound and its Practical Applications: 4-Aiiylanisole as a Bark Beetle Repellent", Chemical Abstracts Service, 1994, pp. 69-79.
Healy et al., "Activation of Anopheles gambiae mosquitoes by carbon dioxide and human breath", Medical Veterinary Entomology, vol. 9, 1995, pp. 331-336.
Healy et al., "Human Sweat and 2-Oxopentanoic Acid Elicit a Landing Response from Anopheles Gambiae", Medical Veterinary Entomology, vol. 14, 2000, pp. 195-200.
Hou et al., "The Effect of Repellents on Penetration into Packaging by Stored-Product Insects", Journal of Stored Products Research, vol. 40, 2004, pp. 47-54.
Hwang et al., "Isolation and Identification of Mosquito Repellents in Artemisia Vulgaris", Journal of Chemical Ecology, vol. 11, No. 9, 1985, 2 pages (English Abstract Submitted).
Ibrahim et al., "Toxicity and Inhibition of Feeding and Tunneling Response of Naphthalene and 10 Derivatives on the Formosan

(56) References Cited

OTHER PUBLICATIONS

Subterranean Termite (Isoptera Rhinotermitidae)", Journal of Economic Entomology, vol. 103, No. 6, Dec. 2010, 2 pages (English Abstract Submitted).
Ihndris et al., "Effect of Promising Insect Repellents on Plastics and Paints", Database Accession No. 1955:86558, vol. 33, No. 7, 2 pages (English Abstract Submitted).
Innocent et al., "Constituents of the Essential Oil of *Suregada zanzibariensis* Leaves are Repellent to the Mosquito, Anopheles Gambiae S.S.", Journal of Insect Science, vol. 10, No. 57, 2010, pp. 1-8.
International Preliminary Report on Patentability received for PCT Patent Application No. PCT/US2011/032804, dated Oct. 26, 2012, 9 pages.
International Preliminary Report on Patentability received for PCT Patent Application No. PCT/US2010/026108, dated Sep. 15, 2011, 8 pages.
International Preliminary Report on Patentability received for PCT Patent Application No. PCT/US2012/060130, dated Apr. 24, 2014, 9 pages.
International Preliminary Report on Patentability received for PCT Patent Application No. PCT/US2012/060673, dated May 1, 2014, 7 pages.
International Preliminary Report on Patentability received for PCT Patent Application No. PCT/US2014/029201, dated Sep. 24, 2015, 8 pages.
International Preliminary Report on Patentability received for PCT Patent Application No. PCT/US2014/029524, dated Sep. 24, 2015, 9 pages.
International Preliminary Report on Patentability received for PCT Patent Application No. PCT/US2016/022998, dated Sep. 28, 2017, 9 pages.
International Search Report and Written Opinion received for PCT Patent Application No. PCT/US2010/026108, dated Oct. 19, 2010, 12 pages.
International Search Report and Written Opinion received for PCT Patent Application No. PCT/US2012/060130, dated Mar. 18, 2013, 13 pages.
International Search Report and Written Opinion received for PCT Patent Application No. PCT/US2012/060673, dated Apr. 1, 2013, 11 pages.
International Search Report and Written Opinion received for PCT Patent Application No. PCT/US2014/029201, dated Oct. 7, 2014, 5 pages.
International Search Report and Written Opinion received for PCT Patent Application No. PCT/US2014/029524, dated Aug. 11, 2014, 5 pages.
International Search Report received for PCT Patent Application No. PCT/US2011/032804, dated Dec. 26, 2011, 5 pages.
International Written Opinion received for PCT Patent Application No. PCT/US2011/032804, dated Dec. 26, 2011, 7 pages.
Invitation to Pay Additional Fees received for PCT Patent Application No. PCT/US2014/029201, dated Jul. 24, 2014, 2 pages.
Jacquin-Joly et al., "Insect Olfactory Receptors: Contributions of Molecular Biology to Chemical Ecology", Journal of Chemical Ecology, vol. 30. No. 12, Dec. 2004, pp. 2359-2397.
Jawara et al., "Field Testing of Different Chemical Combinations as Odour Baits for Trapping Wild Mosquitoes in the Gambia", Plos One, vol. 6, No. 5, 2011, pp. 1-7.
Jones et al., "Allosteric Antagonism of Insect Odorant Receptor Ion Channels", Plos One, vol. 7, No. 1, Jan. 2012, pp. 1-7.
Jones et al., "Two Chemosensory Receptors Together Mediate Carbon Dioxide Detection in *Drosophila*", Nature, vol. 445, Jan. 4, 2007, pp. 86-90.
Jones, Walton, "Olfactory Carbon Dioxide Detection by Insects and Other Animals", Molecules and Cells, vol. 35, 2013, pp. 87-92.
Kain et al., "Retraction: Odour Receptors and Neurons for DEET and New Insect Repellents", Nature, vol. 536, Aug. 25, 2016, p. 488.

Kao et al., "The Biochemical Basis for the Anti-inflammatory and Cytoprotective Actions of Ethyl Pyruvate and Related Compounds", Biochemical Pharmacology, vol. 80, 2010, pp. 151-159.
Karatzoglou et al., "Support Vector Machines in R", Journal of Statistical Software, vol. 15, No. 9, Apr. 2006, pp. 1-28.
Katritzky et al., "Synthesis and Bioassay of Improved Mosquito Repellents Predicted from Chemical Structure", PNAS, vol. 105, No. 21, May 27, 2008, pp. 7359-7364.
Kellogg, F.E., "Water Vapour and Carbon Dioxide Receptors in Aedes Aegypti", J. Insect Physiol., vol. 16, No. 1, 1970, pp. 99-108.
Kline et al., "Olfactometric Evaluation of Spatial Repellents for Aedes Aegypti", Journal of Medical Entomology, vol. 40, No. 4, 2003, pp. 463-467.
Klocke et al., "1, 8-Cineole (Eucalyptol), a Mosquito Feeding and Ovipositional Repellent from Volatile Oil of Hemizonia Fitchii (Asteraceae)", Journal of chemical Ecology, vol. 13, No. 12, 1987, pp. 2131-2141.
Knecht et al., "Distinct Combinations of Variant Ionotropic Glutamate Receptors Mediate Thermosensation and Hygrosensation in *Drosophila*", Elife, vol. 5, e17879, 2016, pp. 1-15.
Knudsen et al., "Diversity and Distribution of Floral Scent", The Botanical Review, vol. 72, No. 1, Mar. 31, 2006, pp. 1-120.
Kovalenko et al., "Repellent Properties of Mannich bases derived from Hydroxy- and Aminobenzoic Acid Esters", Database Accession No. 1983:535492, 1983, 2 pages.
Kreher et al., "Translation of Sensory Input into Behavioral Output via an Olfactory System", Neuron, vol. 59, Jul. 10, 2008, pp. 110-124.
Krzywinski et al., "Analysis of the Complete Mitochondrial DNA from Anopheles Funestus: An Improved Dipteran Mitochondrial Genome Annotation and a Temporal Dimension of Mosquito Evolution", Molecular Phylogenetics and Evolution, vol. 39, 2006, pp. 417-423.
Lacey et al., "Activation, Orientation and Landing of Female Culex Quinquefasciatus in Response to Carbon Dioxide and Odour from Human Feet: 3-D Flight Analysis in a Wind Tunnel", Medical and Veterinary Entomology, vol. 25, 2011, pp. 94-103.
Ldstein et al., "Volatile Constituents from Guava (*Psidium guajava*, L.) Fruit", J. Agric. Food Chem., vol. 33, No. 1, 1985, pp. 138-143.
Leal et al., "Medicinal Alkaloid as a Sex Pheromone", Nature, vol. 385, Jan. 16, 1997, p. 213.
Lee et al., "Avoiding DEET through Insect Gustatory Receptors", Neuron, vol. 67, No. 4, Aug. 26, 2010, pp. 555-561.
Lee et al., "Multiple Gustatory Receptors required for the Caffeine Response in *Drosophila*", Proceedings of the National Academy of Sciences, vol. 106, No. 11, Mar. 17, 2009, pp. 4495-4500.
Linduska et al., "Flea Repellents for Use on Clothing", Journal of Economic Entomology, vol. 39, No. 6, Dec. 1946, pp. 767-769.
Lu et al., "Odor Coding in the Maxillary Palp of the Malaria Vector Mosquito *Anopheles gambiae*", Current Biology, vol. 17, No. 18, Sep. 18, 2007, pp. 1533-1544.
Lyne et al., "Identification of Compounds with Nanomolar Binding Affinity for Checkpoint Kinase-1 using Knowledge-based Virtual Screening", Journal of Medicinal Chemistry, American Chemical Society, vol. 47. No. 8, 2004, pp. 1962-1968.
Mackay et al., "The *Drosophila melanogaster* Genetic Reference Panel", Nature, vol. 482, Feb. 9, 2012, pp. 173-178.
Maldonado et al., "Molecular Similarity and Diversity in Chemoinformatics: From Theory to Applications", Molecular Diversity, vol. 10, 2006, pp. 39-79.
Mann et al., "Sulfur Volatiles from *Allium* Spp. affect Asian Citrus Psyllid, Diaphorina Citri Kuwayama (Hemiptera: Psyllidae), Response to Citrus Volatiles", Bulletin of Entomological Research, vol. 101, 2011, pp. 89-97.
Mason et al., "Anthranilate Repellency to Starlings: Chemical Correlates and Sensory Perception", Journal of Wildlife Management, vol. 53, No. 1, 1989, pp. 55-64.
Masuyama et al., "Mapping Neural Circuits with Activity-Dependent Nuclear Import of a Transcription Factor", J. Neurogenetics, vol. 26, No. 1, 2012, pp. 89-102.
Mayer et al., "Field Evaluation of Non-Pesticide Chemicals as Honey Bee Repellents", Chemical Abstracts Service, Columbus,

(56) References Cited

OTHER PUBLICATIONS

Ohio, US; 2001, XP002744301, Database Accession No. 2001:493021, 2 pages (English Abstract Submitted).
Mboera et al., "The response of Culex Quinquefasciatus (Diptera: Culicidae) to Traps Baited with Carbon Dioxide, 1-Octen-3-ol, Acetone, Butyric Acid and Human Foot Odour in Tanzania.", Bull Entomol Res, vol. 90, No. 2, 2000, pp. 155-159.
Meijerink et al., "Identification of Olfactory Stimulants for Anopheles gambiae from Human Sweat Samples", Journal of Chemical Ecology, vol. 26, No. 6, 2000, pp. 1367-1382.
Mumcuoglu et al., "Repellency of Essential Oils and their Components to the Human Body Louse, Pediculus Humanus Humanus", Entomologia Experimentalis Et Applicata, vol. 78, 1996, pp. 309-314.
Nikonov et al., "A Photoaffinity-Labeled Green Leaf Volatile Compound 'Tricks' Highly Selective and Sensitive Insect Olfactory Receptor Neurons", Chem. Senses, vol. 26, 2001, pp. 49-54.
Njiru et al., "Trapping of the Malaria Vector Anopheles Gambiae with Odour-Baited MM-X Traps in Semi-field Conditions in Western Kenya", Malaria Journal, vol. 5, vol. 39, 2006, pp. 1-8.
Non-Final Office Action received for U.S. Appl. No. 12/398,164, dated Aug. 12, 2013, 12 pages.
Non-Final Office Action received for U.S. Appl. No. 12/398,164, dated Jun. 23, 2011, 10 pages.
Non-Final Office Action received for U.S. Appl. No. 14/351,642, dated Jul. 7, 2016, 17 pages.
Non-Final Office Action received for U.S. Appl. No. 14/352,483 dated Sep. 24, 2015, 6 pages.
Non-Final Office Action received for U.S. Appl. No. 15/279,278, dated Sep. 7, 2017, 8 pages.
Non-Final Office Action received for U.S. Appl. No. 13/641,065, dated Aug. 15, 2014, 9 pages.
Non-Final Office Action received for U.S. Appl. No. 14/855,024, dated Nov. 22, 2016, 8 pages.
Non-Final Office Action received for U.S. Appl. No. 15/672,186, dated Jan. 10, 2019, 15 pages.
Non-Final Office Action received for U.S. Appl. No. 14/853,710, dated Feb. 16, 2017, 9 pages.
Notice of Allowance received for U.S. Appl. No. 12/398,164, dated Sep. 26, 2014, 11 pages.
Notice of Allowance received for U.S. Appl. No. 14/540,908, dated Dec. 4, 2015, 8 pages.
Notice of Allowance received for U.S. Appl. No. 14/352,483, dated Jul. 1, 2016, 7 pages.
Notice of Allowance received for U.S. Appl. No. 14/853,710, dated Aug. 30, 2017, 10 pages.
Notice of Allowance received for U.S. Appl. No. 15/279,278, dated Jan. 2, 2019, 5 pages.
Notice of Allowance received for U.S. Appl. No. 15/279,278, dated Oct. 1, 2018, 9 pages.
Notice of Allowance received for U.S. Appl. No. 15/494,401, dated Sep. 26, 2017, 7 pages.
"Organic Synthesis, vol. III", E.C.Horning, Science Press, Aug. 31, 1981, 2 pages (See Communication under 37 CFR § 1.98(a) (3)).
Paluch et al., "Mosquito Repellents: A Review of Chemical Structural Diversity and Olfaction", Pest Manag Sci., vol. 66, 2010, pp. 925-935.
Patt et al., "Responses of the Asian Citrus Psyllid to Volatiles Emitted by the Flushing Shoots of Its Rutaceous Host Plants", Environmental Entomology, vol. 39, No. 2, Apr. 2010, pp. 618-624.
Pitts et al., "Transcriptome Profiling of Chemosensory Appendages in the Malaria Vector Anopheles Gambiae Reveals Tissue- and Sex-specific Signatures of Odor Coding", BMC Genomics, vol. 12, No. 271, 2011, pp. 1-17.
Pontes et al., "Metasternal Gland Volatiles and Sexual Communication in the Triatomine Bug, *Rhodnius prolixus*", Journal of Chemical Ecology, vol. 34, 2008, pp. 450-457.
Praag et al., "Steam Volatile Aroma Constituents of Roasted Cocoa Beans", Journal of Agricultural and Food Chemistry, vol. 16, No. 6, Nov. 1968, pp. 1005-1008.

Pubchem, "(Pentyl-2 Aminobenzoate, Mar. 26, 2005 CID 100495", Available at:<https://pubchem.ncbi.nlm.nih.gov/compound/100495#section=Top>, pp. 1-15.
Qiu et al., "Attractiveness of MM-X Traps Baited with Human or Synthetic Odor to Mosquitoes (*Diptera: Culicidae*) in the Gambia", Journal of Medical Entomology, vol. 44, No. 6, Nov. 2007, pp. 970-983.
Qiu et al., "Olfactory Coding in Antennal Neurons of the Malaria Mosquito, *Anopheles gambiae*", Chem. Senses, vol. 31, 2006, pp. 845-863.
Ràmia et al., "PopDrowser: The Population *Drosophila* Browser", Bioinformatics, vol. 28, No. 4, 2012, pp. 595-596.
Ramirez et al., "Repellents Inhibit P450 Enzymes in Stegomyia (Aedes) Aegypti", PLOS ONE, vol. 7, No. 11, Nov. 2012, pp. 1-8.
Reeder et al., "Isolation of a Deet-Insensitive Mutant of *Drosophila melanogaster* (Diptera: Drosophilidae)", Journal of Economic Entomology, vol. 94, No. 6, Dec. 2001, pp. 1584-1588.
Rehr et al., "L-Dopa in Legume Seeds: A Chemical Barrier to Insect Attack", Science, vol. 181, Jul. 6, 1973, pp. 81-82.
Restriction Requirement received for U.S. Appl. No. 14/853,710, dated Oct. 31, 2016, 10 pages.
Robertson et al., "Evolution of the Gene Lineage Encoding the Carbon Dioxide Receptor in Insects", Journal of Insect Science, vol. 9, No. 19, 2009, pp. 1-14.
Saito et al., "Odor Coding by a Mammalian Receptor Repertoire", Science Signaling, vol. 2, No. 60, Mar. 3, 2009, pp. 1-14.
Satoh et al., "Absolute Configuration of a New Mosquito Repellent, ( + )-Eucamalol and the Repellent Activity of Its Epimer", Bioscience, Biotechnology, and Biochemistry, vol. 59, No. 6, 1995, pp. 1139-1141.
Schafer Jr. et al., "Acute Oral Toxicity and Repellency of 933 Chemicals to House and Deer Mice", Archives of Environmental Contamination and Toxicology, vol. 14, Jan. 1985, pp. 111-129.
Schmuker et al., "Predicting Olfactory Receptor Neuron Responses from Odorant Structure", Chemistry Central Journal, vol. 1, No. 11, 2007, pp. 1-10.
Scialo et al., "Molecular and Functional Characterization of the Odorant Receptor2 (OR2) in the Tiger Mosquito *Aedes albopictus*", Plos One, vol. 7, No. 5, May 2012, pp. 1-11.
Scognamiglio, "Fragrance Material Review on Cyclopentanone", Food and Chemical Toxicology, vol. 50, 2012, pp. S608-S612.
Sharma et al., "Toxic Effects of Some Plant Oils and Their Common Constituents on the Psyllid Pest, Heteropsylla Cubana (Homoptera:Psyllidae) of Social Forestry Tree *Leucaena leucocephala*", Applied Entomology and Zoology, vol. 27, No. 2, 1992, pp. 285-287.
Shimizu, Yukio, "Adduct ion Formation of Isobutane Chemical Ionization of Aliphatic Olefins", Mass Spectroscopy, vol. 32, No. 4, Oct. 1984, pp. 357-364.
Silbering et al., "Complementary Function and Integrated Wiring of the Evolutionarily Distinct *Drosophila* Olfactory Subsystems", The Journal of Neuroscience, vol. 31, No. 38, Sep. 21, 2011, pp. 13357-13375.
Silbering et al., "Ir40a Neurons are not DEET Detectors", NATURE, vol. 534, Jun. 23, 2016, pp. E5-E7.
Singer, Allen N.., "Topical Hazard Evaluation Program of Candidate Insect", Database Accession No. 1980:141441, 1979, 2 pages.
Smagghe et al., "Insect Cell Culture and Applications to Research and Pest Management", In Vitro Cellular & Developmental Biology—Animal, vol. 45, No. 3, 2009, pp. 93-105.
Smallegange et al., "Effectiveness of Synthetic Versus Natural Human Volatiles as Attractants for Anopheles Gambiae (Diptera: Culicidae) Sensu Stricto", Journal of Medical Entomology, vol. 47, No. 3, May 2010, pp. 338-344.
Smallegange et al., "Host-Seeking Behaviour of Mosquitoes: Responses to Olfactory Stimuli in the Laboratory", Olfaction in Vector-Host Interactions, Chapter. 7, 2010, pp. 143-180.
Smallegange et al., "Sugar-Fermenting Yeast as an Organic Source of Carbon Dioxide to Attract the Malaria Mosquito *Anopheles Gambiae*", Malaria Journal, vol. 9, No. 292, 2010, pp. 1-15.
Smallegange et al., "Synergism Between Ammonia, Lactic Acid and Carboxylic Acids as Kairomones in the Host-seeking Behaviour of the Malaria Mosquito *Anopheles Gambiae Sensu Stricto* (*Diptera: Culicidae*)", Chern. Senses, vol. 30, No. 2, 2005, pp. 145-152.

(56) References Cited

OTHER PUBLICATIONS

Smith et al., "Effectiveness of Repellents Applied to Clothing for Protection against Salt-Marsh Mosquitoes", Journal of Economic Entomology, vol. 42, 1949, 4 pages.

Snow et al., "Swormlure: Development and Use in Detection and Suppression Systems for Adult Screwworm (*Diptera: Calliphoridae*)", Bulletin of the Entomological Society of America, vol. 28, No. 3, Sep. 15, 1982, pp. 277-285.

Su et al., "Non-Synaptic Inhibition Between Grouped Neurons in an Olfactory Circuit", Nature, vol. 492, No. 7427, Dec. 6, 2012, pp. 66-71.

Svirbely et al., "Physical Properties of Some Organic Insect Repellents", Journal of The American Chemical Society, vol. 71, No. 2, Feb. 1949, pp. 507-509.

Sweeney et al., "Targeted Expression of Tetanus Toxin Light Chain in *Drosophila* Specifically Eliminated Synaptic Transmission and Causes Behavioral Defects", Neuron, vol. 14, Feb. 1995, pp. 341-351.

Syed et al., "Acute Olfactory Response of Culex Mosquitoes to a Human- and Bird-derived Attractant", PNAS, vol. 106, No. 44, Nov. 3, 2009, pp. 18803-18808.

Syed et al., "Maxillary Palps Are Broad Spectrum Odorant Detectors in Culex quinquefasciatus", Chem. Senses, vol. 32, 2007, pp. 727-738.

Tanaka et al., "Allyl Derivatives as Cockroach Repellents", Chemical Abstracts Service, Columbus, Ohio, US; Aug. 20, 1975 (Aug. 20, 1975), XP002744424, retrieved from STN Database Accession No. 1976:70350 ; & JP S50 105821 A (Taisho Pharmaceutical Co., I to., Japan; Takasag Perfumery Co.,LTO.) Aug. 20, 1975.

Tanaka et al., "Highly Selective Tuning of a Silkworm Olfactory Receptor to a Key Mulberry Leaf Volatile", Current Biology, vol. 19, No. 11, Jun. 9, 2009, pp. 881-890.

Tentschert et al., "2,3-Dimethyl-5-(2-Methylpropyl)Pyrazine, a Trail Pheromone Component of Eutetramorium Mocquerysi Emery (1899) (Hymenoptera: Formicidae)", Naturwissenschaften, vol. 87, 2000, pp. 377-380.

Turner et al., "Modification of $CO_2$ Avoidance Behaviour in *Drosophila* by Inhibitory Odorants", Nature, vol. 461, Sep. 10, 2009, pp. 277-281.

Turner et al., "Ultra-Prolonged Activation of $CO_2$ -Sensing Neurons Disorients Mosquitoes", Nature, vol. 474, No. 7349, Jun. 2, 2011, pp. 87-91.

Verhulst et al., "Chemical Ecology of Interactions Between Human Skin Microbiota and Mosquitoes", FEMS Microbiol Ecol, vol. 74, 2010, pp. 1-9.

Verhulst et al., "Differential Attraction of Malaria Mosquitoes to Volatile Blends Produced by Human Skin Bacteria", Plos One, vol. 5, No. 12, Dec. 2010, pp. 1-9.

Viktorov-Nabokov et al., "Effect of Substituents in a Series of Benzoic Acid Esters and Amides on Repellence with Respect to Blood-Sucking Mosquitoes", Fiziologicheski Aktivnye Veshchestva vol. 12, 1980, 1 page (Abstract only).

Walker et al., "Quantitative Structure-Activity Relationships for Predicting Percutaneous Absorption Rates", Environmental Toxicology and Chemistry, vol. 22, No. 8, 2003, pp. 1870-1884.

Wang et al., "Molecular Basis of Odor Coding in the Malaria Vector Mosquito *Anopheles gambiae*", PNAS, vol. 107, No. 9, Mar. 2, 2010, pp. 4418-4423.

Wang et al., "QSAR Study of Mosquito Repellents from Terpenoid with a Six-Member-Ring", Bioorganic & Medicinal Chemistry Letters, vol. 18, 2008, pp. 2854-2859.

Wanzala et al., "Chemical Composition and Mosquito Repellency of Essential Oil of Tagetes minuta from the Southern Slopes of Mount Elgon in Western Kenya", Journal of Essential Oil Bearing Plants, vol. 16, No. 2, 2013, pp. 216-232.

Weeks et al., "Topical Hazard Evaluation Program of Candidate Insect Repellent AI3-36706 Pentyl 2-Aminobenzoate", Database Accession No. 1978:1227, Study No. 51-0847-77, Dec. 1977, 13 pages.

Weiss et al., "The Molecular and Cellular Basis of Bitter Taste in *Drosophila*", Neuron, vol. 69, No. 2, Jan. 27, 2011, pp. 258-272.

Whitney, A. W.., "A Direct Method of Nonparametric Measurement Selection", IEEE Transactions on Computers, vol. 20, No. 9, Sep. 1971, pp. 1100-1103.

Xu et al., "Mosquito Odorant Receptor for DEET and Methyl Jasmonate", Proceedings of the National Academy of Sciences, vol. 111, No. 46, Nov. 18, 2014, pp. 16592-16597.

Xue et al., "Field Evaluation of CDC and Mosquito Magnet X Traps Baited with Dry Ice, $CO_2$ Sachet, and Octenol against Mosquitoes", Journal of the American Mosquito Control Association, vol. 24, No. 2, Jun. 2008, pp. 249-252.

Zhu, Song-Nian, "Research on a Repellent for Ants and Rats for Plastics", Chemical Abstracts Service, Columbus, Ohio, US; 2004, XP002744300, Database Accession No. 2004:1027260, 1 page.

Zwiebel et al., "Olfactory Regulation of Mosquito-Host Interactions", Insect. Biochem. Mol. Biol., vol. 34, No. 7, Jul. 2004, pp. 645-652.

Bohbot et al., "Odorant Receptor Modulation: Ternary Paradigm for Mode of Action of Insect Repellents", Neuropharmacology, vol. 62, 2012, pp. 2086-2095.

Boyle et al., "Expanding the Olfactory Code by in Silico Decoding of Odor-Receptor Chemical Space", Elife, vol. 2, 2013, pp. 1-17.

Corbel et al., "Evidence for Inhibition of Cholinesterases in Insect and Mammalian Nervous Systems by the Insect Repellent DEET", BMC Biology, vol. 7, 2009, pp. 1-11.

Ditzen et al., "Insect Odorant Receptors Are Molecular Targets of the Insect Repellent DEET", Science, vol. 319, Mar. 28, 2008, pp. 1838-1842.

Final Office Action received for U.S. Appl. No. 15/073,698, dated Jun. 5, 2017, 10 pages.

Final Office Action received for U.S. Appl. No. 15/694,439, dated Oct. 30, 2018, 9 pages.

International Search Report and Written Opinion received for PCT Patent Application No. PCT/US2016/022998, dated Jun. 21, 2016, 10 pages.

Kain et al., "Odour Receptors and Neurons for DEET and New Insect Repellents", Nature, vol. 502, Oct. 24, 2013, pp. 507-512.

Klun et al., "Comparative Resistance of Anopheles albimanus and Aedes aegypti to N,N-Diethyl-3-methylbenzamide (Deet) and 2-Methylpiperidinyl-3-cyclohexen-1-carboxamide (AI3-37220) in Laboratory Human-Volunteer Repellent Assays", Journal of Medical Entomology, vol. 41, No. 3, May 2004, pp. 418-422.

Krajick, Kevin, "Medical entomology. Keeping the Bugs at Bay", Science, vol. 313, No. 5783, Jul. 7, 2006, pp. 36-38.

Liu et al., "Distinct Olfactory Signaling Mechanisms in the Malaria Vector Mosquito *Anopheles Gambiae*", Plos Biology, vol. 8, No. 8, Aug. 2010, pp. 1-17.

Non-Final Office Action received for U.S. Appl. No. 15/073,698, dated Oct. 4, 2016, 12 pages.

Non-Final Office Action received for U.S. Appl. No. 15/694,439, dated Mar. 22, 2018, 11 pages.

Pellegrino et al., "A Natural Polymorphism Alters Odour and DEET Sensitivity in an Insect Odorant Receptor", Nature, vol. 478, Sep. 21, 2011, pp. 511-514.

Stanczyk et al., "Behavioral Insensitivity to DEET in Aedes Aegypti is a Genetically Determined Trait Residing in Changes in Sensillum Function", PNAS, vol. 107, No. 19, May 11, 2010, pp. 8575-8580.

Syed et al., "Generic Insect Repellent Detector from the Fruit Fly *Drosophila melanogaster*", Plos One, vol. 6, No. 3, Mar. 2011, pp. 1-6.

Syed et al., "Mosquitoes Smell and Avoid the Insect Repellent DEET", PNAS, vol. 105, No. 36, Sep. 9, 2008, pp. 13598-13603.

Tauxe et al., "Targeting a Dual Detector of Skin and $CO_2$ to Modify Mosquito Host Seeking", Cell, vol. 155, No. 6, Dec. 5, 2013, pp. 1365-1379.

Ulrich et al., "Analysis of Strawberry Flavour—Discrimination of Aroma Types by Quantification of Volatile Compounds", Zeitschrift für Lebensmitteluntersuchung und—Forschung A, vol. 205, 1997, pp. 218-223.

Xia et al., "The Molecular and Cellular Basis of Olfactory-Driven Behavior in Anopheles Gambiae Larvae", PNAS, vol. 105, No. 17, Apr. 29, 2008, pp. 6433-6438.

(56) References Cited

OTHER PUBLICATIONS

Dean, (2009). "An Environmentally Friendly Mosquito Repellent?" Available Online at <https://dotearth.blogs.nytimes.com/2009/08/26/an-environmentally-friendly-mosquito-repellent/>, 3 pages.

Deepa et al., (2010). "Bioinsecticidal Compounds of Celastraceae—the Spindle Tree Family," International Journal of Botany, 6:220-227.

EPPO Global Database, (2002). "Diaphorina citri (DIAACI)", Available online at <https://gd.eppo.int/taxon/DIAACI>, 1 page.

Final Office Action received for U.S. Appl. No. 15/672,186, dated Jul. 23, 2019, 15 pages.

Final Office Action received for U.S. Appl. No. 15/851,130, dated Jan. 21, 2020, 9 pages.

ITIS Report, (2021). "Heteropsylla cubana", available online at <https://www.itis.gov/servlet/SingleRpt/SingleRpt?search_topic=TSN&search_value=200482#null>, 2 pages.

Klun et al., (2001). "Stereochemical Effects in an Insect Repellent," Journal of Medical Entomology, 38:809-812.

Malerbo-Souza et al., (2004). "Efficiency of n-Octyl-Acetate, 2-Heptanone and Citronellal in Repelling Bees from Basil (*Ocimum sellowii-Labiatae*)," Brazilian Archives of Biology and Technology, 47:121-125.

Non-Final Office Action received for U.S. Appl. No. 15/851,130, dated Jul. 9, 2019, 6 pages.

Notice to File Missing Parts received for U.S. Appl. No. 17/105,283, dated Dec. 9, 2020, 2 pages.

Percy, (2009). "Psyllids of Economic Importance," Available online at <https://www.psyllids.org/psyllidsPests.htm>, 7 pages.

Pohlit et al., (2011). "Patent Literature on Mosquito Repellent Inventions which Contain Plant Essential Oil—A Review," Planta Medica, 77:598-617.

Yoon et al., (2007). "Repellent Efficacy of Caraway and Grapefruit Oils for Sitophilus oryzae (Coleoptera: Curculionidae)," Journal of Asia-Pacific Entomology, 10:263-267.

* cited by examiner

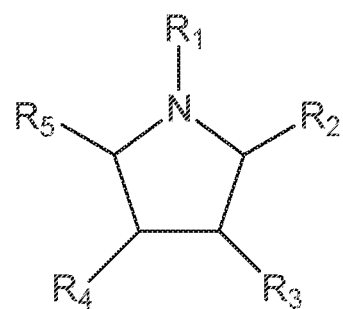
(I)
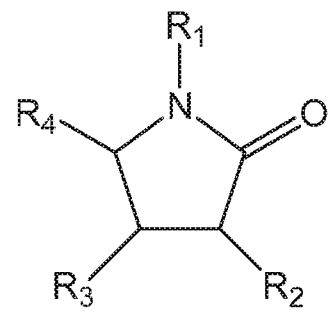
(II)
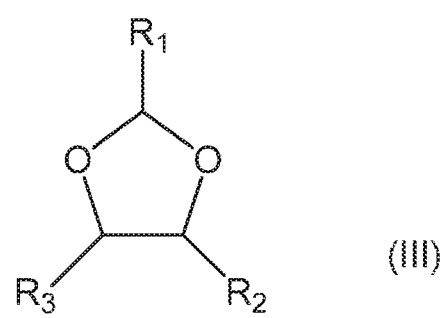
(III)
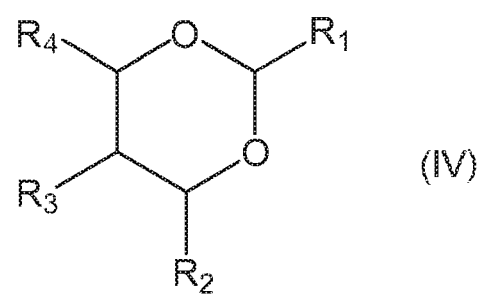
(IV)
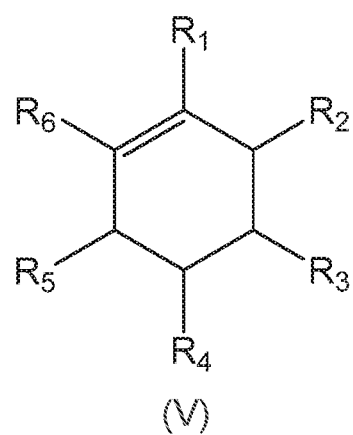
(V)
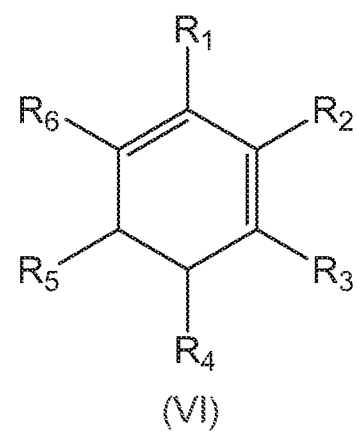
(VI)
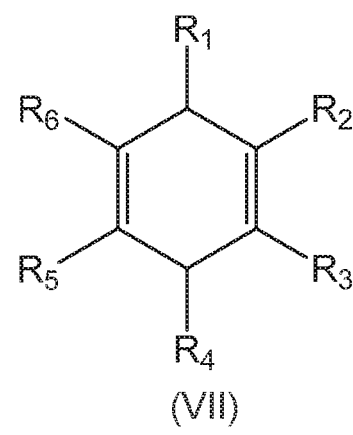
(VII)
FIG. 1A

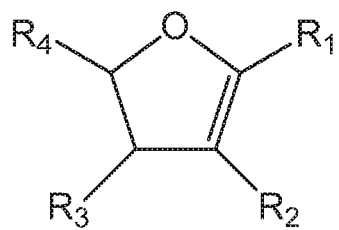
(VIII)
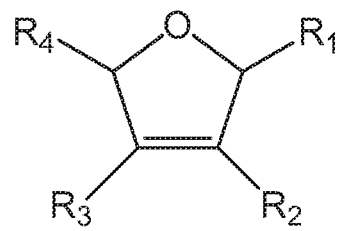
(IX)
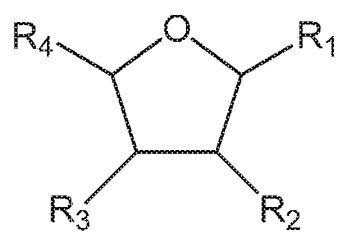
(X)
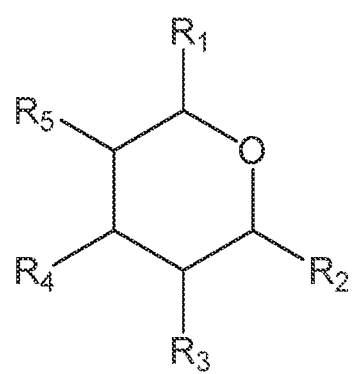
(XI)
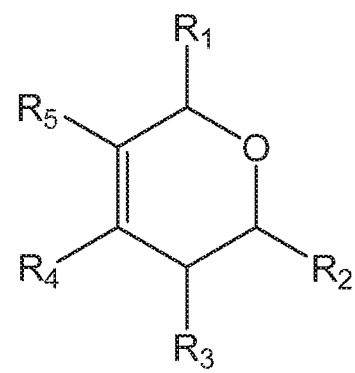
(XII)
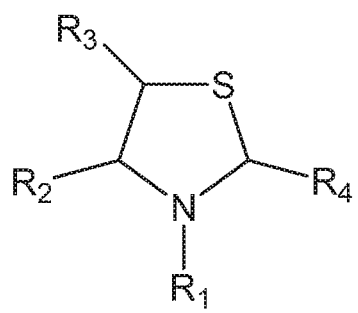
(XIII)
FIG. 1B

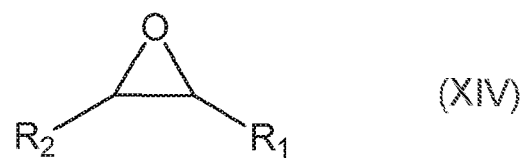
(XIV)
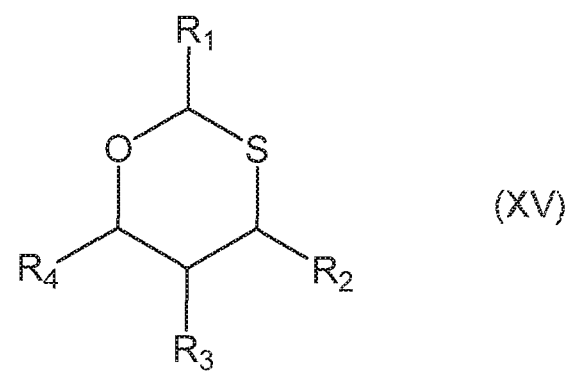
(XV)
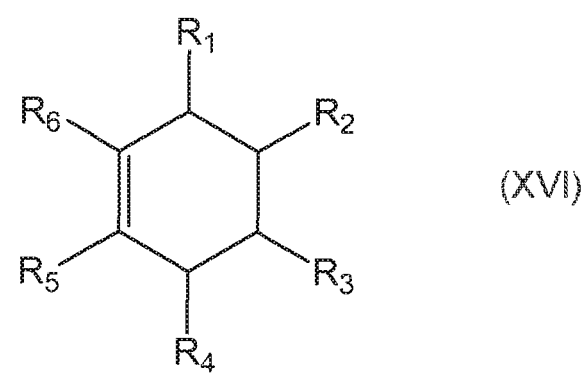
(XVI)
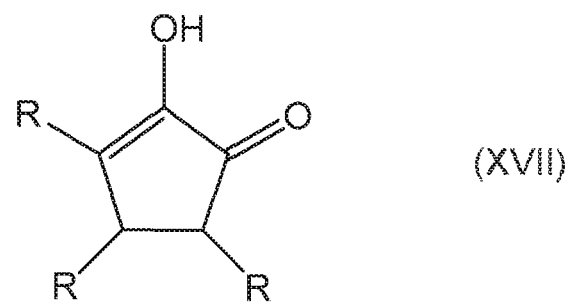
(XVII)
FIG. 1C

| Chemical genus | Structure | SMILES | CAS NO | NAME | computed DISTANCE FROM 4-methylpiperidine |
|---|---|---|---|---|---|
| 3 | O=C1N(CCC)CCC1 | O=C1N(CCC)CCC1 | 74048-20-7 | 1-propyl-2-pyrrolidone | 1.690295968 |
| 3 | O=C1N(CC)CCC1 | O=C1N(CC)CCC1 | 2687-91-4 | 1-ethyl-2-pyrrolidone | 1.817911476 |
| 3 | O=C(O)[C@H]1NCCC1 | O=C(O)[C@H]1NCCC1 | 18875-45-1 | L-proline | 1.842821675 |
| 3 | O=C(O)C1N(O)CCC1 | O=C(O)C1N(O)CCC1 | 18610-59-8 | (S)-4-hydroxyproline | 1.969754424 |
| 3 | O=C1N(CCC1)C=C | O=C1N(CCC1)C=C | 9003-39-8 | polyvinyl pyrrolidone | 2.077455945 |

FIG. 3A

| | | | | |
|---|---|---|---|---|
| 4 | C(CC1C(OC1)(C)C | CC1CCSCC1 | 5161-17-1 | 4-methyl thiane | 1.549992324 |
| 5 | CC1C(CCO1)S | C(O)C1OC(OC1)(C)C | 100-79-8 | acetone glycerol | 1.565752093 |
| 5 | C(CC1CCCO1)CC | CC1OCCC(O1)C | 766-20-1 | 2,4-dimethyl-1,3-dioxane | 1.697837349 |
| 5 | CC1(SSCC1)C | C[C@H]1OC[C@@H](O)CO1 | 3674-23-5 | cis-5-hydroxy-2-methyl-1,3-dioxane | 1.755317457 |

FIG. 3B

| | | | | |
|---|---|---|---|---|
| 5 | 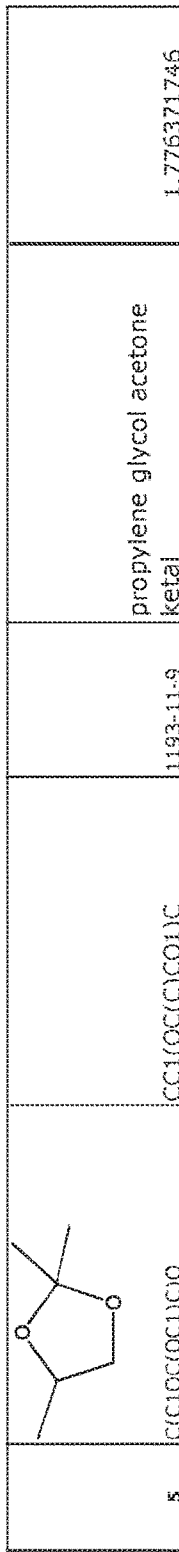 | CC1(OC(C)CO1)C | 1193-11-9 | propylene glycol acetone ketal | 1.776371746 |
| 5 | 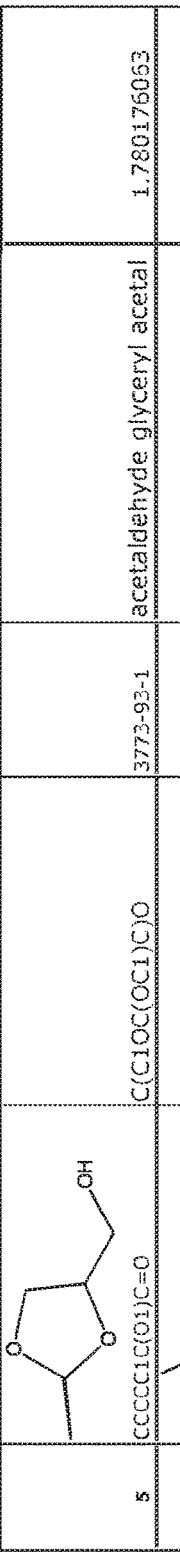 | C(C1OC(OC1)C)O | 3773-93-1 | acetaldehyde glyceryl acetal | 1.780176053 |
| 5 |  | CC1C(C)OC(CC)O1 | 24382-63-6 | 2-ethyl-4,5-dimethyl-1,3-dioxolane | 1.834143177 |
| 5 | 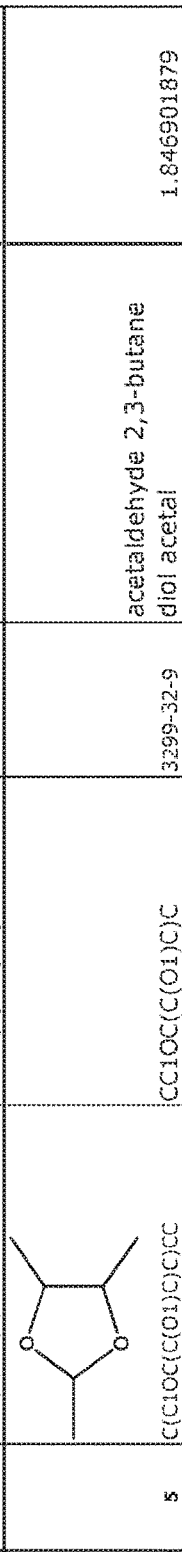 | CC1OC(C(O1)C)C | 3299-32-9 | acetaldehyde 2,3-butane diol acetal | 1.846901879 |
| 5 | 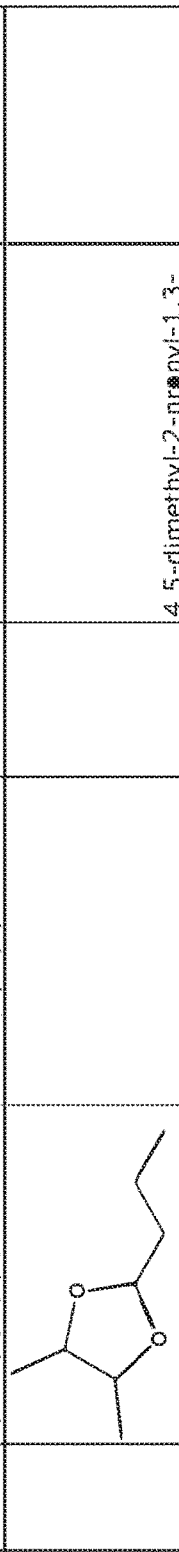 | C(C1OC(C(O1)C)C)CC | 6414-34-2 | 4,5-dimethyl-2-propyl-1,3-dioxolane | 1.84789495 |
| 5 | 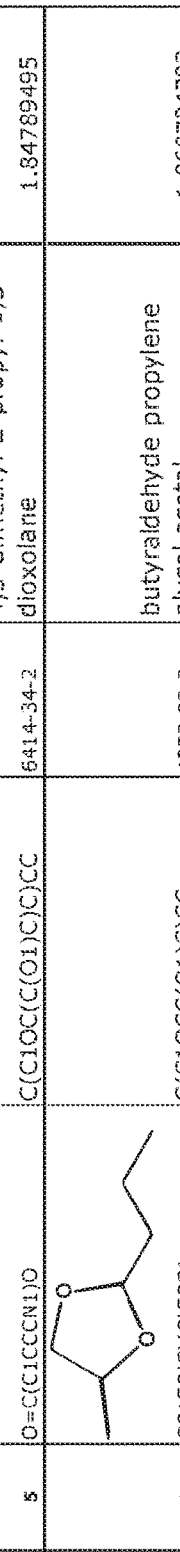 | C(C1OCC(O1)C)CC | 4352-99-2 | butyraldehyde propylene glycol acetal | 1.868704793 |
FIG. 3C

| | | | | |
|---|---|---|---|---|
| 5 | O=C(C1=CCCN1)C | C(C)CCC1OC(CO1)C | 74094-60-3 | valeraldehyde propylene glycol acetal | 1.87309748 |
| 5 | CC1(OC(CO1)C)C(O)C | C(C1OC(CO1)C)C | 4359-46-0 | 2-ethyl-4-methyl-1,3-dioxolane | 1.902946281 |
| 5 | C(C(C(CC)C)CC1)O | CC1(OC(CO1)C)C(O)C | 94089-23-3 | acetoin propylene glycol acetal | 1.905554384 |
| 5 | O=C1NCCCC1 | CC1OCC(O1)C | 3390-12-3 | propylene acetal | 1.933990555 |
| 5 | CC1=C(C(CC1)=O)O | CC1COC(O1)C(C)C | 67879-60-1 | isobutyraldehyde propylene glycol acetal | 1.987716122 |
| 5 | C(C1OCCC1)OC(CC)=O | C(C1OCC(O1)C)CC | 18433-93-7 | isovaleraldehyde propylene glycol acetal | 2.013306833 |

FIG. 3D

| | | | | |
|---|---|---|---|---|
| 6 | CC1=CCC=CC1 | 4313-57-9 | 1-Methyl-1,4-cyclohexadiene | 1.859871038 |
| 6 | CC1=CCCC=C1 | 1489-57-2 | 2-methyl-1,3-cyclohexadiene | 1.970689511 |
| 6 | CC1=CC=CCC1 | 30640-46-1 | lemon hexadiene | 1.872559533 |
| 6 | CC1=CC=CCC1 | 1489-56-1 | 1-methyl-1,3-cyclohexadiene | 1.872559533 |
| 6 | O=C1C(=CCCC1)O | 10316-66-2 | 2-hydroxy-2-cyclohexenone | 1.972493855 |
| 6 | CC(C)C1CCC(=CC1)C(C)O | 18479-68-0 | para-menth-1-ene-9-ol | 2.084153252 |

FIG. 3E

| | Structure | SMILES | CAS | Name | Value |
|---|---|---|---|---|---|
| ? | (structure) CC1CO1 | C(C1OC(=C(O)C1=O)C)C | 27538-10-9 | ethyl furaneol | 2.089625999 |
| ? | (structure) CC1OC(=C(O)C=C1)C | C(C1=C(C(C(=O)O1)=O)C)C | 27538-09-5 | shoyu furanone | 2.110227452 |
| ? | (structure) CC1OC(=C(O)C1=O)C | C(C1OC(=O)C=C1)C | 2407-43-4 | 2-hexen-4-olide | 2.120332898 |
| ? | (structure) CC1OC(=C(O)C1=O)C | CC1OC(=C(O)C1=O)C | 131222-82-7 | (R)-strawberry furanone | 2.121260262 |
| ? | (structure) C(C1OC(=O)C=C1)CCC | CC1OC(=C(O)C1=O)C | 131222-81-6 | (S)-strawberry furanone | 2.121260262 |

FIG. 3F

| | Structure | SMILES | CAS | Name | Value |
|---|---|---|---|---|---|
| 7 | 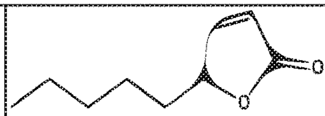 | C(CCCC)CCO C(C1OC(=O)C=C1)CCCC | 21963-26-8 | 5-pentyl-5H-furan-2-one | 2.121395179 |
| 8 | | CC1C(CCO1)S | 57124-87-5 | 2-methyl-3-tetrahydrofuran thiol | 1.591477875 |
| 8 | | C(C1CCCO1)O C(C1CCCO1)O | 97-99-4 | tetrahydrofurfuryl alcohol | 1.597034541 |
| 8 | | OCC1OCCC1 OCC1OCCC1 | 93842-55-8 | Tetrahydro-2-furanmethanol | 1.597034541 |
| 8 | | CC1CCCOC1 CC1CCCOC1 | 26093-63-0 | (ÃƒÂ¢Ã©Å¡Ã‚Â±)-3-methyl tetrahydropyran | 1.597491026 |
| 8 | | CC1C(CCO1)O O=C1N(CCC)CCC1 | 29848-44-0 | 2-methyl tetrahydro-3-furanol | 1.616163001 |

FIG. 3G

| | | | | |
|---|---|---|---|---|
| 8 | [structure] | CC1=CC(S)CS1 | 1004-29-1 | 2-butyl tetrahydrofuran | 1.70168497 |
| 8 | [structure] | O=C1N(CC)CCC1 | 17108-52-0 | 2,5-dimethyl-2,3-dihydrofuran | 1.817435987 |
| 8 | [structure] | C(O)C1CC(C=C(C1)C)C | 110-87-2 | dihydropyran | 1.822636399 |
| 8 | [structure] | O=C(O)[C@H]1NCCC1 | 96-47-9 | 2-methyl tetrahydrofuran | 1.842666234 |
| 8 | [structure] | CC1CCCC=C1 | 142-68-7 | tetrahydropyran | 1.843650896 |
| 8 | [structure] | C(C1OCC(O1)C)CC | 53897-26-0 | 5,6-dihydro-2H-pyran-2-carbaldehyde | 1.861508079 |

FIG. 3H

| | | | | | |
|---|---|---|---|---|---|
| 8 | [structure] C(C1OCC(O1)C)(C)C | C/C=C/C1C(C)C(C)CCO1 | 990113 | TETRAHYDRO-METHYL-METHYLPROPENYL-PYRAN | 2.011209987 |
| 8 | [structure] | C(C1OCCC1)OC(CC)=O | 637-65-0 | tetrahydrofurfuryl propionate | 2.035141823 |
| 8 | [structure] O=C1N(CCC1)C=C | O=C1COC(C)C1 | 34003-72-0 | 5-methyl tetrahydrofuran-3-one | 2.106353793 |
| | [structure] O=C1CCCC(C)O1 | | | | |
| 9 | [structure] | O=C1CCCC(C)C(C)O1 | 10413-18-0 | 5,6-dimethyl tetrahydropyran-2-one | 2.106527146 |
| 9 | [structure] C(C1=C(C(C(C)O1)=O)C | CC1=CCOC(C)C=C(C)C | 1786-08-9 | nerol oxide | 2.146872863 |
| | C(O)CCCSC | | | | |

FIG. 3I

| | SMILES | CAS | Name | Value |
|---|---|---|---|---|
| 9 | CC1CC(OCC1)C=C(C)C | CC(C)=CC1OCCC(C1)C | 5258-11-7 | (-)-(E)-rose oxide | 2.153750796 |
| 9 | CC1CC(OCC1)C=C(C)C | CC1CC(OCC1)C=C(C)C | 16409-43-1 | (Z)-rose oxide | 2.153750796 |
| 10 | CC1C(CCO)O | C(C1NCCS1)CC | 24050-10-0 | 2-propyl thiazolidine | 1.610438725 |
| 10 | C/C=C/C1C(C)C(C)CCO1 | CC(C)CC1SCC=N1 | 39800-92-5 | 2-isobutyl-3-thiazoline | 2.005978713 |
| 10 | CC(C)CCO | SCCN1CSCC1 | 317803-83-5 | N-(2-mercaptoethyl)-1,3-thiazolidine | 2.149834874 |

FIG. 3J

| | | | | |
|---|---|---|---|---|
| 11 | CC1=NC(C)O1 | 56079-02-8 | 4-mercapto-2-methyl-4,5-dihydrothiophene | 1.705750492 |
| 11 | ![structure] CC1(OC(C)CO1)C | 58384-57-9 | 3,3-dimethyl-1,2-dithiolane | 1.757878983 |
| 11 | ![structure] CC1=CCCC=C1 | 51288-07-4 | 2,2,4-trimethyl-1,3-dithiane | 1.870028172 |

FIG. 3K

| | | | | |
|---|---|---|---|---|
| 12 | | C(C@H]1OC[C@@H]1O)C01 C(C1CO1)CCCC | 5063-65-0 | heptylene oxide | 1.746924273 |
| 12 | | C(C1SC(OCC1)CC CCCCC1C(O1)C=O | 58936-30-4 | 2,3-epoxyheptanal | 1.789031533 |
| 12 | | CC1=CCC(O1)C CCCCCC1C(O1)C=O | 42134-50-9 | 2,3-epoxyoctanal | 1.799630845 |
| 12 | | C1C=COCC1 C(C1CO1)CCC | 1436-34-6 | hexylene oxide | 1.822188659 |
| 12 | | C(C1=C(O1)C(=O)CC1C C(C1OC1)C=C)C(=O)C | 78307-41-2 | 4,5-epoxy-2-heptenal | 1.943017557 |
| 12 | | C(C)CCCO CC1CO1 | 75-56-9 | propylene oxide | 2.092950592 |

FIG. 3L

| | | | | |
|---|---|---|---|---|
| 13 | [structure] | C(C1SC(OCC1)C)CC | 59323-76-1 | cis-galbanum oxathiane | 1.793686832 |
| 13 | [structure] | CC1(C)SC(C)OCC1 | 72472-02-7 | 2,4,4-trimethyl-1,3-oxathiane | 1.837752113 |
| | [structure] | CC1CCC=CC1 | | | |
| 14 | [structure] | CC1CCCO1 | 591-47-9 | 4-methyl cyclohexene | 1.83867744 |
| 14 | [structure] | CC1OC(C(O)C)C | CC1CCCC=C1 | 591-48-0 | 3-methyl cyclohexene | 1.843805489 |

FIG. 3M

| | | | | |
|---|---|---|---|---|
| 14 | ![structure] | CC1CC(C)OC(CC)O1 | 67634-16-6 | 2,4-dimethyl-3-cyclohexene-1-methanol | 1.825652488 |
| 15 | ![structure] | C(C1=C(O)C(=O)CC1)C | 21835-01-8 | ethyl cyclopentenolone | 1.952419904 |
| 15 | ![structure] | CC1=C(C(CC1)=O)O | 80-71-7 | cyclotene hydrate | 1.996730481 |
| 16 | ![structure] | C(C1C(CC(C)CC1)O)O | 68480-15-9 | floral methanol | 1.925953792 |

FIG. 3N

| | | | | |
|---|---|---|---|---|
| 17 | (structure) | CC1=CCOC(C1)C=C(C)C | C1=CC=CC2=C1NCCC2 | 635-46-1 | 1,2,3,4-tetrahydroquinoline | 2.142710005 |
| 18 | (structure) | O=C(C1=CCCCN1)C | CC1C=NC(C)O1 | 6159-22-4 | 2,5-dimethyl-3-oxazoline | 1.71082925 |
| 19 | (structure) | O=C1N(C)C(C)CN1 | O=C(C1=CCCCN1)C | 25343-57-1 | 6-acetyl-1,2,3,4-tetrahydropyridine | 1.733557783 |
| 20 | (structure) | C(C1CO1)CCCC | O=C1N(C)C(C)CN1 | 80-73-9 | DIMETHYL IMIDAZOLIDINONE | 1.741439855 |

FIG. 30

ARTHROPOD REPELLENT CHEMICALS

CROSS REFERENCE TO RELATED APPLICATIONS

This application is a continuation of U.S. patent application Ser. No. 15/694,439, filed on Sep. 1, 2017, which is a continuation of U.S. patent application Ser. No. 15/073,698, filed on Mar. 18, 2016, which claims priority benefit of U.S. Provisional Application No. 62/134,882, filed on Mar. 18, 2015, the disclosures of each of which are hereby incorporated by reference in their entireties.

STATEMENT REGARDING FEDERALLY SPONSORED RESEARCH OR DEVELOPMENT

This invention was made with Government support under Grant No. 1R01DC014092-01A1 from the National Institutes of Health. The Government has certain rights in this invention.

BACKGROUND

Field of the Invention

The invention relates to chemicals and methods for repelling arthropods.

Related Art

Mosquitoes and other blood-feeding insects transmit deadly diseases such as malaria, dengue, lymphatic filariasis, West Nile fever, Yellow fever, sleeping sickness and Leishmaniasis to hundreds of millions of people, causing untold suffering and more than a million deaths every year. In addition, these diseases cause significant morbidity throughout the globe and the daily adjusted life in years (DALY) caused by malaria alone is >25M, implying that new control approaches may have substantial impact in preventing sicknesses transmitted by mosquito bites. Current methods such as insecticide treated bednets provide the main line of protection, however effective insect behavior control methods could provide an additional line of defense for more individuals in an abode, perhaps even protecting outdoors, and diminish concerns associated with heavy insecticide use such as health and emergence of resistance.

N,N-Diethyl-m-toluamide (DEET) has remained the primary insect repellent used for more than 60 years in the developed world but has very little use in disease control in Africa and Asia due to a high relative cost and the inconvenience of requiring continuous application to skin at high concentrations (30-100%). DEET has been shown to inhibit mammalian cation channels and human acetylcholinesterase, which is also a target of carbamate insecticides [1] that are commonly used in disease-endemic areas, increasing concerns about prolonged use. Several instances of increased resistance to DEET have also been reported in flies [2], *Anopheles albimanus* [3], and *Aedes aegypti* [4]. Moreover, DEET is a solvent and melts several forms of plastics, synthetic fabrics, painted and varnished surfaces [5].

SUMMARY

In one aspect, a composition for repelling an arthropod is provided. The arthropod-repelling composition comprises a carrier, and one or any combination of arthropod repellant compounds that are structurally unrelated and discovered by novel cheminformatic algorithms that were created to understand the biochemical, spacial charge density and many other biochemical and physical factors aside from straight chemical structure for imparting the activity to known repellents such as DEET, picaridin, para-menthane-diol, geraniol, citronella, butyl anthranilate, ethyl anthranilate, and ethyl pyruvate, and then using that novel information to identify whole classes of structurally novel molecules that can be shown to demonstrate repellant activity surprisingly across a unexpectedly broad range of arthropods and not just a few species of mosquitoes.

In some embodiments, the arthropod-repelling composition comprises a carrier, and one or any combination of arthropod repellant compounds selected from the group consisting of a thiane compound, a pyrrolidone compound, a cyclohexadiene compound, a cyclohexenone compound, a cyclohexene compound, a furanone compound, a pyran compound, a tetrahydropyran compound, a thiazolidine compound, a thiazoline compound, a dihydrothiophene compound, a dithiolane compound, a dithiane compound, an epoxide compound, an oxathiane compound, a cyclopentene compound, a cyclohexane compound, a quinoline compound, an oxazoline compound, a tetrahydropyridine compound, and an imidazolidinone compound.

In some embodiments, the arthropod repellant compounds are selected from the group of compounds listed in FIG. 1, or a combination thereof. Thus, the composition can comprise one or any combination of arthropod repellant compounds selected from:

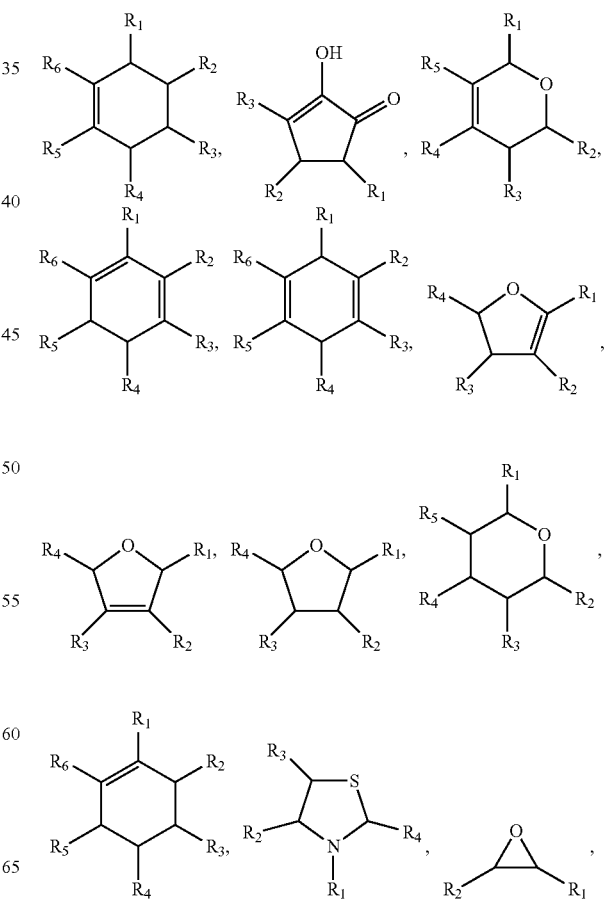

-continued

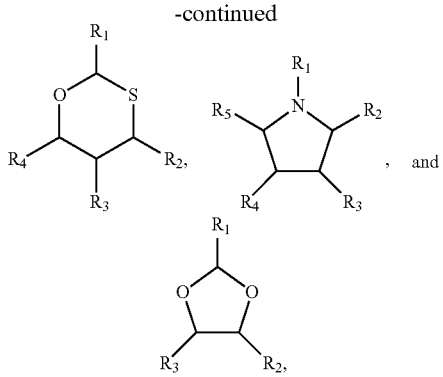

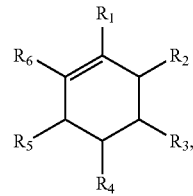

wherein $R_1$ is H, alkyl, or hydroxyl; $R_2$ is H or hydroxyl; $R_3$, $R_5$, and $R_6$ are each H; and $R_4$ is H, alkyl, or alkoxy. In some embodiments, $R_1$ is a $C_1$-$C_6$ alkyl, $R_4$ is a $C_1$-$C_6$ alkyl or a $C_1$-$C_6$ alkoxy, or any combination thereof.

or a pharmaceutically acceptable or environmentally acceptable salt thereof, wherein $R_1$, $R_2$, $R_3$, $R_4$, $R_5$, $R_6$, $R_7$ and $R_8$ are each independently selected from the group consisting of H, O, alkyl, alkenyl, aryl, arylalkyl, alkoxy, an aldehyde group, benzoyl, formyl, cycloalkyl, an ester group, halo, hydroxyl, alkoxycycloalkylalkyl, cycloalkenyl, and cycloakenylalky. In certain embodiments, the alkyl is a $C_1$-$C_{12}$ alkyl, the alkenyl is a $C_2$-$C_{12}$ alkenyl, the alkoxy is a $C_1$-$C_{12}$ alkoxy, the aldehyde group is a $C_1$-$C_{12}$ aldehyde group, the ester group a $C_1$-$C_{12}$ ester group, or any combination thereof.

In some embodiments, the arthropod-repelling composition comprises particular embodiments of the compounds listed in FIG. 1. Thus, arthropod repellant compounds can be selected from the group consisting of 4-methylcyclohexene, ethyl cyclopentenolone, 3,4-Dihydro-2H-pyran, and lemon hexadiene.

In some embodiments, the arthropod-repelling composition comprises particular embodiments of the compounds listed in FIG. 1. Thus, the arthropod repellant compound can be selected from the following compounds, or a pharmaceutically acceptable or environmentally acceptable salt thereof:

a)

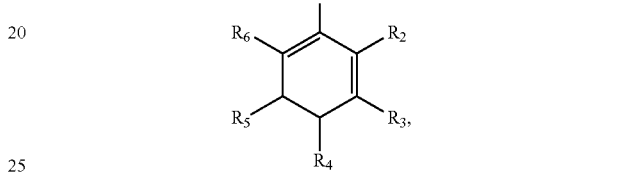

wherein $R_3$, $R_4$, and $R_5$ are each H; $R_1$ is H, alkyl or alkenyl; and $R_2$ is H or O. In some embodiments, the alkyl is a $C_1$-$C_6$ alkyl, and the alkenyl is a $C_1$-$C_6$ alkenyl.

b)

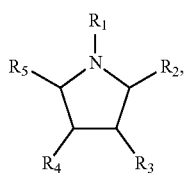

wherein $R_1$, $R_2$ and $R_3$ are each independently H, alkyl, alkenyl, or alkoxy. In some embodiments, the alkyl is a $C_1$-$C_6$ alkyl, the alkenyl is a $C_1$-$C_6$ alkenyl, and the alkoxy is a $C_1$-$C_6$ alcohol.

c)

wherein $R_1$, $R_4$, $R_5$ and $R_6$ are each H; and $R_2$ and $R_3$ are each independently H or alkyl. In some embodiments, the alkyl is a $C_1$-$C_6$ alkyl.

d)

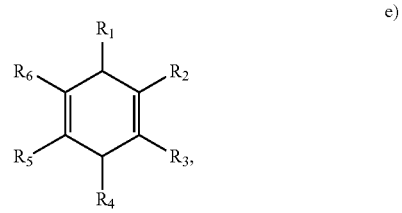

wherein $R_1$, $R_3$, $R_4$, $R_5$ and $R_6$ are each H; and $R_2$ is H or alkyl. In some embodiments, the alkyl is a $C_1$-$C_6$ alkyl.

e)

f)

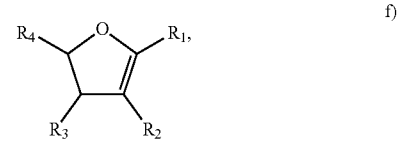

wherein $R_1$, $R_2$, and $R_4$ are each independently H, hydroxyl, or alkyl; and $R_3$ is H or O. In some embodiments, the alkyl is a $C_1$-$C_3$ alkyl.

g)

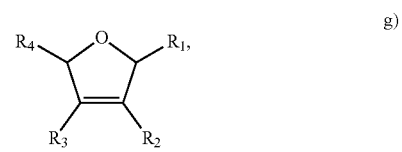

wherein $R_2$ and $R_3$ are each H; and $R_1$ and $R_4$ are each independently H, O or alkyl. In some embodiments, the alkyl is a $C_1$-$C_6$ alkyl.

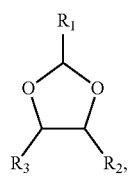

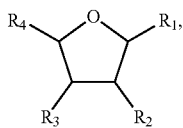
h)

wherein $R_3$ and $R_4$ are each H; $R_1$ is SH, hydroxyl, alkyl, alkoxy or an ester group; and $R_2$ is H, O or OH. In some embodiments, the alkyl is a $C_1$-$C_6$ alkyl, the alkoxy is a $C_1$-$C_4$ alkyl, and the ester group is a $C_1$-$C_6$ ester group.

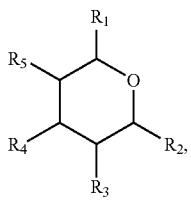
i)

wherein $R_3$ is H; $R_1$, $R_4$ and $R_5$ are each independently H or $CH_3$; and $R_2$ is H or alkyl.

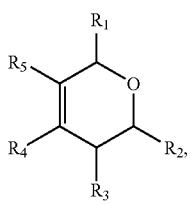
j)

wherein $R_1$, $R_3$ and $R_5$ are H; and $R_2$ and $R_4$ are each independently a branched or unbranched alkyl. In some embodiments, the branched or unbranched alkyls is $C_2$-$C_6$ branched or unbranched alkyl.

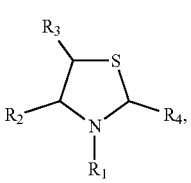
k)

wherein $R_2$ and $R_3$ are each H; and $R_1$ and $R_4$ are each independently alkyl or an aldehyde group. In some embodiments, the aldehyde group is a $C_2$-$C_6$ aldehyde group.

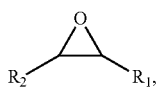
l)

wherein $R_1$ and $R_2$ are each independently H, alkyl, or an aldehyde group. In some embodiments, the aldehyde group is a $C_2$-$C_6$ aldehyde group.

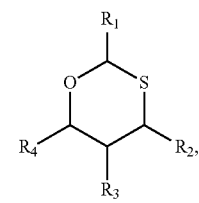
m)

wherein $R_3$ and $R_4$ are each H; and $R_1$ and $R_2$ are each independently H, alkyl, or an aldehyde group. In some embodiments, the aldehyde group is a $C_2$-$C_6$ aldehyde group.

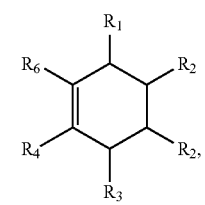
n)

wherein $R_1$, $R_2$, $R_3$, $R_4$, $R_5$ and $R_6$ are each independently H, O, alkyl, alkenyl, aryl, arylalkyl, alkoxy, an aldehyde group, benzoyl, formyl, cycloalkyl, an ester group, halo, hydroxyl, alkoxycycloalkylalkyl, cycloalkenyl, or cycloakenylalky; or

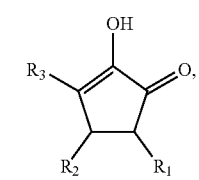
o)

wherein $R_3$ is H, alkyl, or an aldehyde group, and $R_1$ and $R_2$ are each H. In some embodiments, $R_3$ is a $C_2$-$C_6$ aldehyde group.

In more particular embodiments of the arthropod-repelling composition, the arthropod repellant compounds can be any compound listed in Table 1 of FIG. 3.

In some embodiments, the arthropod-repelling composition comprises one arthropod repellant compound, two arthropod repellant compounds, or more than two arthropod repellant compounds. Thus, in some embodiments, the composition can comprise one, two, or more than two, arthropod repellant compounds.

In some embodiments, the arthropod repellant compounds can be selected from the group consisting of 1,2-epoxyhexane, 1-methyl-1,4-cyclohexadiene, 1-ethyl-2-pyrrolidone, 2-isobutyl-4-methyl-1,3-di oxolane, 2-methyl tetrahydrofuran, 3,4-Dihydro-2H-pyran, 4-hydroxy-2,5-dimethyl-3 (2H)-furanone, 4-methyl cyclohexene, dihydropyran, ethyl cyclopentenolone, isopropyl quinoline, methyl 2-(4-tert-butylphenyl)acetate, and nerol oxide, or a pharmaceutically acceptable or environmentally acceptable salt thereof.

In some embodiments, the arthropod-repellant compounds can be selected from the group consisting of 2-butyl-4,6-dimethyl-5,6-dihydro-2H-pyran, 2-methyl-4-methylidene-6-phenyloxane, 1-methylpyrrolidin-2-one, 10-undecen-1-al, 3-ethyl-2-hydroxycyclopent-2-en-1-one, 1-methyl-1,3-cyclohexadiene, alpha cedrene epoxies, floral methanol, 4,5-epoxy-(E)-2-decenal, oxyquinoline, isobutyl quinolone, 6-methoxyquinoline, 6-methyl quinolone, quinmerac, 4-amino-5-(3-(isopropyl amino)-2,2-dimethyl-3-oxopropoxy)-2-methyl quinoline-3-carboxylic acid, 1-methyl cyclohexene, 3-methyl cyclohexene, mixed cyclohexene, furanone acetate, and 2-methylquinoline, or a pharmaceutically acceptable or environmentally acceptable salt thereof.

In embodiments of any of the arthropod-repelling compositions: a) the arthropod can be from a broad range of members of arthropods such as insect, tick, mite, spider, centipede or scorpion; b) the arthropod can be a blood-feeding arthropod, which can be a mosquito, gadfly, louse, bedbug, sandfly, blackfly, tsetse fly, midge, mite, or flea; c) the arthropod can be a household or agricultural pest; or d) any combination of a)-c).

In another aspect, a method of repelling an arthropod is provided. The method includes exposing an arthropod to any of the above described arthropod-repelling compositions in an amount effective to repel the arthropod. In some embodiments, when the compositions and arthropod repellant compounds are applied to living material (such as skin, fruit, plants, and the like), the arthropod repellant compound or compounds can range in concentration between about 0.5% to about 50% vol/vol of the formulation, or about 0.5% to about 50% wt/vol of the formulation, depending on whether the formulation is liquid-based or lotion-based. In certain embodiments, the concentration can be about 0.5% to about 15% vol/vol of the formulation or about 0.5% to about 15% wt/vol of the formulation. When applied on non-living material (such as fabric, net, surfaces, and the like), the concentration of the repellant compound can range from about 1% to about 100% vol/vol of the formulation, or about 1% to about 100% wt/vol of the formulation, depending on the formulation. In certain embodiments, the concentration can be about 0.5% to 15% vol/vol of the formulation or about 0.5% to 15% wt/vol of the formulation.

In some embodiments of the method: a) the arthropod is exposed to the arthropod-repelling composition by applying the composition to a subject, to an article worn by the subject, to an article associated with the subject, to an agricultural product, to a storage container, shipping container or transport container for an agricultural product, to a structure or part of a structure from which the arthropod is to be repelled, or to an area from which the arthropod is to be repelled; b) the subject can be an animal or a plant; c) the subject can be a human; d) the arthropod can be an insect, tick, mite, spider, centipede or scorpion; e) the arthropod can be a blood-feeding arthropod, which can be a mosquito, gadfly, louse, bedbug, sandfly, blackfly, tsetse fly, midge, mite, or flea; f) the arthropod can be a household or agricultural pest, or any combination thereof; or g) any combination of a)-f).

BRIEF DESCRIPTION OF THE DRAWINGS

For a more complete understanding of the present invention, reference is now made to the following descriptions taken in conjunction with the accompanying drawings, in which:

FIGS. 1A-1C are respective parts of a panel of chemical compounds for repelling an arthropod, wherein $R_1$, $R_2$, $R_3$, $R_4$, $R_5$, $R_6$, $R_7$ and $R_8$ are each independently selected from the group consisting of H, O, alkyl, alkenyl, aryl, arylalkyl, alkoxy, an aldehyde group, benzoyl, formyl, cycloalkyl, an ester group, halo, hydroxyl, alkoxycycloalkylalkyl, cycloalkenyl, and cycloakenylalky.

FIGS. 3A-3O are respective parts of a Table 1 of predicted novel repellents grouped according to similar chemical functional groups.

DETAILED DESCRIPTION

Figure 2:
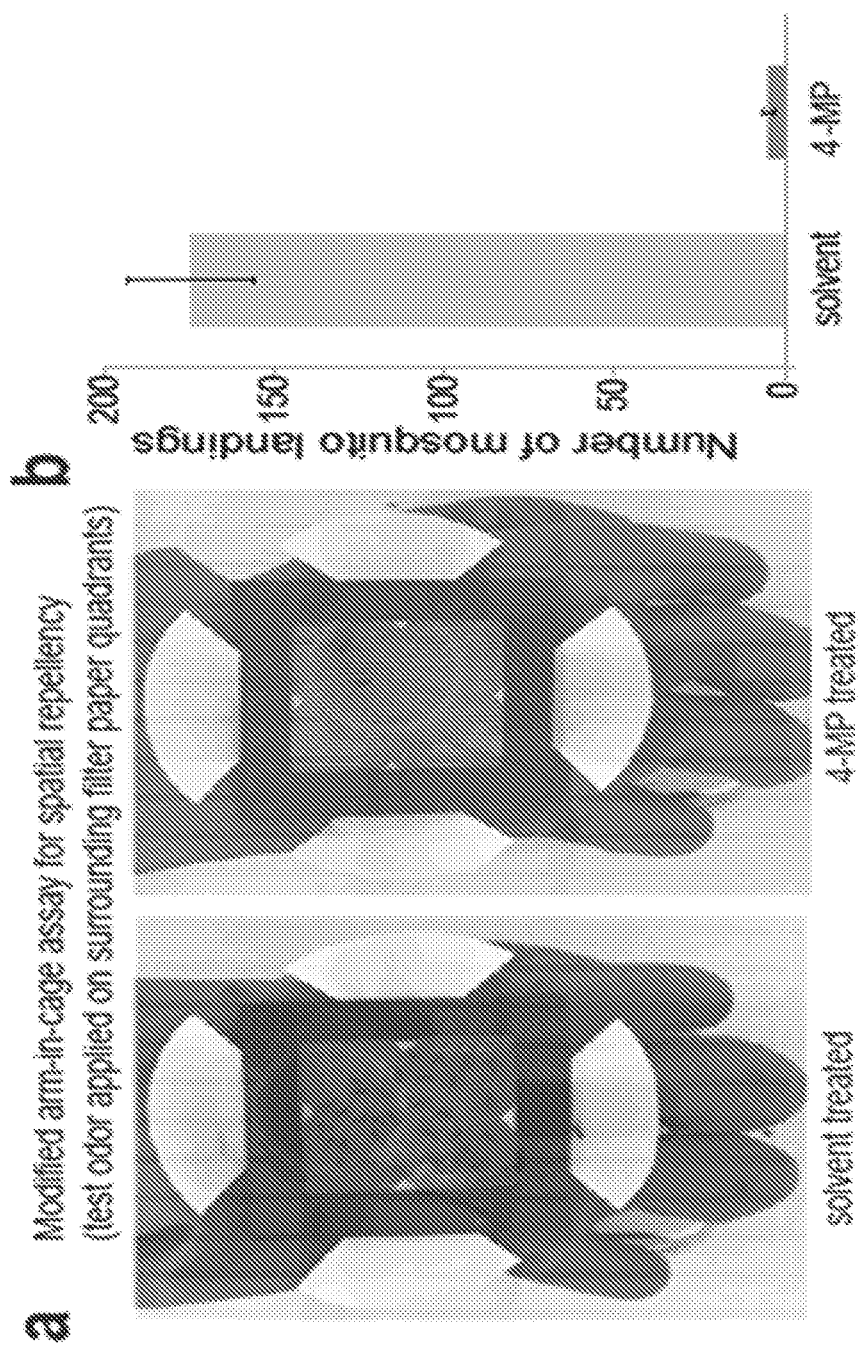
FIG. 2 is a panel of representative photographs of modified arm-in-cage assay testing of 4-MP (4%) with Aedes aegypti females. (2a) Control and 4-MP treated gloves; (2b) Mean numbers of landings within minutes 2-5 of the assay. N=4 trials, ~40 mosquitoes/trial.

In one aspect, compositions for repelling arthropods are provided that comprise one or more arthropod repellant compounds. In some embodiments, the composition also comprises one or more carriers, which can be dermatologically acceptable or environmentally acceptable carriers, or a combination thereof.

The term "alkyl" refers to a branched or unbranched saturated hydrocarbon group such as, but not limited to, methyl, ethyl, n-propyl, isopropyl, n-butyl, isobutyl, t-butyl, octyl, and decyl. The term "cycloalkyl" refers to a saturated cyclic hydrocarbon group such as, but not limited to, cyclopentyl and cyclohexyl. In some embodiments, an alkyl group can be a $C_{1-12}$ alkyl group.

The term "alkenyl" refers to a branched or unbranched hydrocarbon group containing at least one double bond, such as, but not limited to, ethenyl, n-propenyl, isopropenyl, n-butenyl, isobutenyl, octenyl, and decenyl. The term "cycloalkenyl" refers to a cyclic hydrocarbon group containing at least one double bond such as, but not limited to, cyclopentenyl and cyclohexenyl. In some embodiments, an alkenyl group can be a $C_{1-12}$ alkenyl group.

The term "aryl" refers to an aromatic hydrocarbon group containing a single aromatic ring or multiple aromatic rings that are fused together, linked covalently, or linked to a common group such as a methylene or ethylene moiety. In some embodiments, aryl groups contain one aromatic ring or two fused or linked aromatic rings such as, but not limited to, phenyl, naphthyl, biphenyl, diphenylether, diphenylamine, and benzophenone. In particular embodiments, an aryl group including any substituents can have from 4 to 50 carbon atoms, 4 to 40 carbon atoms, 4 to 30 carbon atoms, 4 to 20 carbon atoms, or 4 to 10 carbon atoms, or more particularly, can have from 6 to 50 carbon atoms, 6 to 40 carbon atoms, 6 to 30 carbon atoms, 6 to 20 carbon atoms or 6 to 10 carbon atoms.

The term "arylalkyl" refers to an alkyl group with an aryl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "functional group" refers to any reactive substituent. Examples of functional groups include, but are not limited to, hydroxy, cyano, halo, nitro, ester, ether, amino and carboxy groups.

The term "alkoxy" refers to an alkyl group bound through a single, terminal ether linkage; that is, an "alkoxy" group may be represented as —O-alkyl where alkyl is as described above.

The term "alkoxycycloalkylalkyl" refers to a cycloalkylalkyl group where at least one of the hydrogen atoms of the cycloalkyl group is replaced by an alkoxy group. Examples of alkoxycycloalkylalkyl groups include, but not limited to, cyclopropylmethoxymethyl and 4-methoxycyclohexylmethyl.

The term "cycloalkenylalkyl" means an alkyl as described above which is substituted by a cycloalkenyl as described above. Examples of cycloalkenylalkyl groups include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, and 1-(1-cyclopenten-1-yl)hexyl.

In some embodiments, the arthropod-repelling composition is used against harmful insects, including those that are directly or indirectly detrimental to humans, for example blood-feeding insects, parasitic insects, pathogenic insects, stinging insects, poisonous insects and generally disagreeable insects. Blood-feeding insects include mosquitoes, gadfly, lice, bedbugs and so on. Parasitic insects include fleas and lice, and pathogenic insects include flies, mosquitoes, croton bugs and lice. Stinging insects include bees, reduviidae species, and poisonous insects include ghungbannalkye, cerambycidae species and Spanish fly. Disagreeable insects include Chironominae, gagiworm and stinkbug.

In some embodiments, the arthropod-repelling compositions can be used against arthropods such as ticks, spiders, centipedes and scorpions.

The arthropod can be an arthropod plant pest, an arthropod crop pest, or an arthropod household pest. Examples of plant and crop pests include, but are not limited to, Spotted wing *Drosophila*, Asian citrus psyllid, Asian longhorned beetle, European grapevine moth, European gypsy moth, light brown apple moth, Mediterranean fruit fly, Mexican fruit fly, oriental fruit fly, khapra beetle, boll weevil, and white fly, soft scales; examples of household pests include, but are not limited to, ants, cockroaches, and termites.

Thus, the arthropod-repelling compositions can be used against arthropods that carry diseases responsible for health or economic loss in humans, pets, crops or livestock.

In some embodiments, the arthropod-repelling composition can contain two or more arthropod repellent compounds. In some embodiments, a repellent composition can be used against two or more different arthropods.

In some embodiments, a subject to be treated with a repellant compound can be a human or animal subject (e.g., dogs, cats, horses, cattle). Animal subjects include pets, livestock, and poultry. Subjects can be directly or indirectly treated, such as by applying the active compound to the skin of the subject, or by applying the active compound to an article worn by or otherwise protecting the subject.

In other embodiments, the subject is a plant, which can include ornamentals and agricultural crop plants. The plants can be treated in the field, in greenhouses, in storage, and in transit. Repellant compounds can be applied to the plant, or to edible or to inedible plant products.

Formulations for application to a human or animal subject can be prepared with the use of customary auxiliary skin-compatible and pharmacologically unobjectionable substances and additives. Such additives may be, for example, emulgators, solvents, thickeners, fillers, stabilizers, preservation agents or antioxidants. Moreover, surfactants such as polyoxy ethylene sorbitan acid and esters or salts of bile acid may also be used to improve bio-availability. Dispersion agents such as polyacrylate, lignin, tannates or derivatives thereof may be added to enable insoluble substances to be incorporated. Hydrogels can be produced with the aid of hydrophilic organic solvents such as glycerine, glycol or aliphatic alcohols, for example. Furthermore, active agents can be used in the form of active substance-containing microsomes or liposomes or as liposomally or microsomally capsuled active agents, which can be in parallel with other auxiliary substances and further active agents.

Formulations and compositions may be processed to obtain practically all forms of preparations suited for application to the human or animal skin, such as tinctures, hydrogels, oil-in-water emulsions, water-in-oil emulsions, suspensions, solutions, lotions, pastes, creams, gels, ointments, powders, sprays, and the like. Delivery devices such as patches, clothing, bracelets, hats, and other articles in contact with a subjects skin and containing one or more arthropod repellant compounds are also contemplated.

Exemplary cosmetically acceptable and/or dermatologically acceptable carriers that can be included in a formulation or composition include such substances as aqueous or non-aqueous solutions, suspensions, and emulsions. In the case of pastes, creams or gels, examples of the carriers include, but are not limited to, animal oil, vegetable oil, wax, paraffin, starch, tragacanth, cellulose derivative, polyethylene glycol, silicon, bentonite, silica, talc, and zinc oxide. In the case of powders or sprays, examples of the carriers include, but are not limited to, lactose, talc, silica, aluminum hydroxide, calcium silicate, and polyamide power. For sprays, a propellant such as chlorofluorohydrocarbon, propane/butane or dimethylether can also be included. In the case of solutions or emulsions, examples of the carriers include, but are not limited to, solvents, solubilizers and emulsifiers such as water, ethanol, isopropanol, ethyl carbonate, ethyl acetate, benzyl alcohol, benzyl benzoate, propylene glycol, 1,3-butylglycol oil, glycerol fatty acid ester, polyethylene glycol and sorbitan fatty acid ester. In the case of suspensions, examples of the carriers include, but are not limited to, liquid diluents such as water, ethanol and propylene glycol, suspending agents such as ethoxylated isostearyl alcohol, polyoxyethylene sorbitol ester and polyoxyethylene sorbitan ester, microcrystalline cellulose, aluminum methahydroxide, bentonite, agar, and tragacanth.

In some embodiments, the arthropod-repelling composition or compound can be applied to an article such as luggage, a bed frame, or the like. In other embodiments, the repellant composition or compound can be applied to a structure or part of a structure, such as a house, window frame, closet, tent, greenhouse, storage shed, or the like. In some embodiments, the repellant composition or compound can be applied to an area, such as a field, garden, yard, outdoor area, or the like. In some embodiments, the repellant composition or compound can be applied to a container such as a storage container, shipping container or transport container, or the like. In some embodiments, the repellant composition or compound can be applied to agricultural and food products such as fruits, vegetables, stored products, stored feed products, prepared foods and food products, prepared feed products, and the like.

For application to articles, structures, areas, agricultural produces, and the like, that are environmentally acceptable formulations and repellant composition can be prepared in any known manner, for instance by extending the compositions with conventional pesticide dispersible liquid diluent carrier and/or dispersible solid carriers, optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. Suitable liquid diluents or carriers include, but are not limited to, water, petroleum distillates, or other liquid carrier with or without surface active agents. The choice of dispersing and emulsifying agents and the amount employed is dictated by the nature of the composition and the ability of the agent to facilitate the dispersion of the compositions. Non-ionic, anionic, amphoteric, or cationic dispersing and emulsifying agents may be employed, for example, but not limited to, the condensation products of alkylene oxides with phenol and organic acids, alkyl aryl sulfonates, complex ether alcohols, quaternary ammonium compounds, and the like.

Examples of carriers include, but are not limited to, an inert or fluid material, which may be inorganic or organic and of synthetic or natural origin, with which an active compound is mixed or formulated to facilitate its application to the skin or hair or other object to be treated, or its storage, transport and/or handling. In general, any of the materials customarily employed in formulating pesticides, herbicides, or fuigicides, are suitable. Embodiments of the compositions and repellant compounds may be employed alone or in the form of mixtures with such solid and/or liquid dispersible carrier vehicles and/or other known compatible active agents such as other pesticides, or pediculicides, acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. Depending on the expected use, embodiments of the compositions can be formulated as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules. Also, formulation used with burning equipment, such as fumigating cartridges, fumigating cans and fumigating coils, as well as ULV cold mist and warn mist formulations, are contemplated.

In some embodiments, formulations and arthropod-repelling compositions can be applied to a subject's skin, or can be applied to garments, belts, collars, or other articles worn by the subject from whom insects or other arthropods are to be repelled. In some embodiments, a formulation or repellant composition can be applied to netting or screening that protects a subject, particularly a sleeping subject. In some embodiments, a formulation o repellant composition can be applied to non-human/non-animal subjects from which arthropods are to be repelled, such as plants. Application to a subject can be carried out by spraying, dusting, sprinkling, pouring, dipping, and the like. In some embodiments, a repellant composition or formulation can be applied to an area of pest infestation or an area susceptible to infestation, such as, but not limited to, a body of water, a container, a barn, a carpet, or pet bedding.

The utility of this novel cheminformatic approach is that the resulting algorithms can be used to identify novel and effective repellents otherwise not known or anticipated to those skilled in the art which chemicals have a variety of different physicochemical properties and safety-to-humans/pets/plants potentially leading to the development of close-to-contact repellents for topical application as well as farther-from-source ones for short range repellency. The vapor pressures of such compounds are predicted to have a large range, opening the possibility for use in different formulations such as body lotions, skin creams, washing detergents, perfumes, on clothes, bednets, house entryways, backyards, etc.

Since the processes that appear to be impacted by these novel repellants appear to be conserved across fly and mosquito species, this new generation of repellents may also be used tackle disease transmission by other disease vectors and plant pests that cause severe morbidity, mortality, and economical losses. Additionally, since these new repellents are structurally different from DEET and other current commercial repellants they may be effective against DEET-resistant strains.

The present invention may be better understood by referring to the accompanying examples, which are intended for illustration purposes only and should not in any sense be construed as limiting the scope of the invention.

Example 1

The first major limitation to finding effective DEET substitutes was that the molecular targets through which it causes repellence in adult mosquitoes were unknown. Past studies had put forward competing models about mechanisms of DEET action, but demonstration of a causal relationship to repellency was lacking [4, 6-11]. The second major limitation in developing improved repellents is the cost of the screening and development process to find new repellants based on classical screening of existing compounds in trials with mosquito's and proxies for their targets. This is expensive. It has been suggested that >$30M and several years may be required for identification and subsequent human-safety analyses of new repellent chemistries [15]. In a novel breakthrough the inventors developed a powerful cheminformatics descriptor-based prediction algorithm that allowed for digitally screening >400,000 compounds (including 3000 natural compounds) based on the previously described cheminformatics platform, and have identified >100 natural compounds as candidate repellents that are previously unknown to have insect repellant activity. These chemicals do not dissolve plastic, are affordable, have pleasant odors, and several are already shown as safe for human use. They simply were never anticipated to be broadly active arthropod repellants.

The identification of these compounds started with understanding the biochemical, spacial charge density and other biochemical and physical factors aside from straight chemical structure for imparting the activity with existing DEET-like chemical structure and are therefore studying just DEET-like properties there were limits in finding completely novel classes of repellents that are not structurally related to DEET. Additional properties were then added. Another class of repellent identified previously has been 4methyl piperidine, and because it is more volatile than DEET, proof-of-principle experiments were performed to test whether it can act as a non-contact repellent that does not require being in close proximity to be effective, such as DEET. Olfactory avoidance to DEET is active over a short range (~1 cm) and mosquitoes are not repelled beyond the immediate vicinity. Therefore, a modified arm-in-cage assay was developed where a low concentration of 4-MP can be applied to filter paper pieces adjoining the netted landing window of the glove (FIG. 2a). It was found that 3% 4-methyl piperidine can effectively repel mosquitoes from the skin-exposed net window (FIG. 2b). These experiments indicate that identification of additional compounds from the inventors' novel algorithms that have biochemical, metabolic and other properties that allow them to interact with the arthropod receptors controlling repellency behavior in a broad range of arthropods is possible but that the inventors could also 'instruct' their novel algorithms to include a search for novel compounds that also have practical physical parameters such as varying levels of volatility that will provide valuable product performance characteristics as there is a great need to find novel repellants that could protect from a distance.

Example 2

A list of compounds for inclusion in embodiments of the invention are shown in Table 1 of FIG. 3. These compounds are predicted by novel algorithms of the inventors using the aforementioned parameters and are expected to have arthropod repellent activity. The compounds were identified by a cheminformatics prediction method, as follows:

In order to identify novel chemicals with repellent properties a chemical informatics method was utilized for identification of select physicochemical descriptors that are correlated with chemical structure showing a specific activity. Using Sequential Forward Selection and a set of Dragon physicochemical descriptors was identified that correlated with repellency values of one set of known repellents. Next, these descriptors were utilized to rank computational distance from 4-methylpiperidine. It was anticipated that this unusual approach would give several classes of chemicals that would be distinct in chemical functional groups and structure with repellent properties.

A set of training compounds were utilized, including a non-repellent set of odors that were assigned protection efficacy to zero, and the repellents DEET, Picaridin, butyl anthranilate and ethyl anthranilate, were assigned the highest value since the assumption was made that these would have various properties important for repellence. A compound-by-compound repellency distance matrix was generated from the known repellency data of the training set. A separate compound-by-compound descriptor distance matrix was calculated using the 3,224 descriptor values calculated by the Dragon software package. A Sequential Forward Selection (SFS) approach was then used, where each of the 3224 descriptor were individually tested and selected if they were able to increase the correlation between descriptor values of compounds in training set and their repellency values. This process is continued until no further improvements in correlation occur. This resulted in a unique and novel descriptor set that is optimized for anticipating repellency in compounds heretofore unanticipated to impact repellent behaviour by people skilled in the art. This repellency-optimized descriptor set was utilized to rank computational distance from 4-methylpiperidine amongst compounds from a natural compound library of ~12000 volatiles identified from the scientific literature as being present in food, cosmetic, fragrances, plant, animal or insect origin. A selection of compounds falling within the computed distance of 0-2.3 from 4-methyl piperidine (<1% of all compounds) were identified and manually inspected for chemical functional groups that are distinct from known repellents like 4-methylpiperidine, DEET, Picaridin, butyl anthranilate and ethyl anthranilate and listed as predicted repellents as listed in Table 1.

The distance from 4-methypiperidine is computed using the descriptors and represents the Euclidian distance.

Example 3

In order to test the repellency prediction rate of the computational approach to find structurally new functional groups of chemicals, ~15 of these various classes of compounds in Table 1 were randomly selected. These chemicals were tested in behavioral assays to determine percentage success rate of the computational predictions. The three behavior assays and their results are described below and they measured repellency involved 2 species of insects: *Drosophila melanogaster* and *Aedes aegypti*. Overall the rate of success for significant repellency to either one of these species is indicated by a negative value for Preference Index (P.I.)

T-maze assay was used to test selected compounds. 4-7 day old starved wild-type flies of *Drosophila melanogaster* (20 males plus 20 females/trial) were tested. Under a chemical hood, 10 ul of solvent and 10 ul of test chemical were applied onto filter paper placed in control tubes and test tubes. The flies were loaded into the elevator of a T-maze apparatus and lowered into position where they could make a choice between the solvent tube and the test chemical tube. After allowing flies to make choice for 1 minute in dark, the elevator was closed and number of flies in each tube was counted. Preference Index (P.I.)=(#flies in test arm−#flies in control arm)/(#flies in test arm+#flies in control arm). The results presented in Table 2 report the average Preference Index from 3 independent trials. It was demonstrated that 5 of the 6 compounds tested were repellent as shown in Table 2.

TABLE 2

*Drosophila melanogaster* T-maze assay with compounds at 5% concentration

| Compound | P.I. | S.E.M. |
|---|---|---|
| 3.4-Dihydro-2H-pyran | −0.88 | 0.07 |
| 1-methyl-1,4-cyclohexadiene | −0.76 | 0.14 |
| 2-Isobutyl-4-methyl-1,3-dioxolane | −0.3 | 0.17 |
| 1,2-Epoxyhexane | −0.2 | 0.13 |
| Isopropyl quinolone | −0.17 | 0.13 |
| Propylene glycol acetone ketal | −0.09 | 0.14 |

Mean preference index (P.I) of *Drosophila melanogaster* to the tested compounds in the T-maze assay.
Negative preference index indicates repellency.
S.e.m. = standard error of mean.

Example 4

In a second type of assay, a *Drosophila melanogaster* 2-choice trap assay as described previously[4,6] was used with minor modifications. Traps were made with two 1.5 ml microcentrifuge tubes (USA Scientific) and 200 microliter pipette tips (USA Scientific), each cap contained standard cornmeal medium. T-shape piece of filter paper (Whatman #1) was impregnated with 5 ul of acetone (control) or 5 microliters of 5% test odor, diluted in acetone. Traps were placed within a petri dish (100×15 mm, Fisher) containing 10 ml of 1% agarose to provide moisture. Ten wild-type *Drosophila melanogaster* flies 4-7 days old were used per trial, which lasted 48 hours by which time point nearly all flies in the assays had made a choice and were counted. Preference Index (P.I.)=(number of flies in treated trap−number in control trap)/(number of flies in treated+control traps). We demonstrate that 4 of 4 compounds tested were repellent as shown in Table 3.

TABLE 3

*Drosophila melanogaster* 2-choice Trap assay with compounds at 5% concentration

| Compound | P.I. | S.E.M. |
|---|---|---|
| 1,2,3,4-Tetrahydroquinoline | −0.74 | 0.13 |
| 4-Hydroxy-2,5-Dimethyl-3(2H)-Furanone | −0.24 | 0.45 |

TABLE 3-continued

Drosophila melanogaster 2-choice Trap
assay with compounds at 5% concentration

| Compound | P.I. | S.E.M. |
|---|---|---|
| methyl 2-(4-tert-butylphenyl)acetate | −0.14 | 0.43 |
| 1-Ethyl-2-pyrrolidone | −0.12 | 0.44 |

Mean preference index (P.I) of Drosophila melanogaster to the tested compounds in the 2-choice trap assay.
Negative preference index indicates repellency.
S.e.m. = standard error of mean.

Example 5

In order to test the compounds in mosquitoes, a Two-choice heat assay in Aedes aegypti was performed. A pair of heat sources were prepared using 2 hand warmers fitted into a 100×15 mm petri dish base and covered with 15×15 cm polyester netting secured round the petri dish by a pair or 8 inch plastic cable ties (Gardner Bender, Milwaukee, Wis.) coupling. Excess netting material was trimmed off round the edges of the petri dish. The treatment chemical 500 µl was added at 3% concentration directly onto the netting and the two assembled dishes were placed inside a cage of 20 female A. aegypti mosquitoes. Total numbers of mosquito landings on the net covering of each dish were counted during the assay from video recordings of the 5 minute trial. The solvent and DEET positions were alternated between runs. The results are presented in Table 4.

TABLE 4

Aedes aegypti 2-choice landing assay
with compounds at 3% concentration

| Compound | P.I. | S.E.M. |
|---|---|---|
| 1,2,3,4-tetrahydroquinoline | −0.996494303 | 0.002479 |
| 4-methyl cyclohexene | −0.82646711 | 0.04096 |
| Ethyl cyclopentenolone | −0.742280162 | 0.056252 |
| Dihydropyran | −0.281907175 | 0.009002 |
| 2-isobutyl-4-methyl-1,3-dioxalane | −0.218927924 | 0.002592 |
| 2-methyl tetrahydrofuran | −0.181488683 | 0.062167 |
| 1-Methyl-1,4-cyclohexadiene | −0.158403379 | 0.036229 |
| Nerol Oxide | −0.035619389 | 0.014402 |

Mean preference index (P.I) of female Aedes aegypti to the tested compounds in the 2-choice trap assay.
Two heat sources at 37 C. are used as attractants.
Negative preference index indicates repellency.
S.e.m. = standard error of mean.

Example 6

In order to test the compounds in mosquitoes, a Two-choice heat assay in Aedes aegypti was performed. A pair of heat sources were prepared using 2 hand warmers fitted into a 100×15 mm petri dish base and covered with 15×15 cm polyester netting secured round the petri dish by a pair or 8 inch plastic cable ties (Gardner Bender, Milwaukee, Wis.) coupling. Excess netting material was trimmed off round the edges of the petri dish. The treatment chemical 500 µl was added at 3% concentration directly onto the netting and the two assembled dishes were placed inside a cage of 20 female A. aegypti mosquitoes. Total numbers of mosquito landings on the net covering of each dish were counted during the assay from video recordings of the 5 minute trial. The solvent and DEET positions were alternated between runs. The results are presented in Table 5.

TABLE 5

Aedes aegypti 1-choice landing assay
with compounds at 3% concentration

| Chemical | Average % Repellency | S.E.M. |
|---|---|---|
| 1,2,3,4-tetrahydroquinoline | 99.8240985 | 0.175901 |
| Isopropyl Quinoline | 96.36376901 | 1.700953 |
| 4-methyl cyclohexene | 90.38873654 | 3.476294 |
| Ethyl cyclopentenolone | 77.43655406 | 15.41482 |
| 2-isobutyl-4-methyl-1,3-dioxalane | 35.91990601 | 0.493366 |
| 2-methyl tetrahydrofuran | 29.77948258 | 12.66656 |
| 1-Methyl-1,4-cyclohexadiene | 27.01016447 | 7.65119 |
| Nerol Oxide | 6.804131568 | 3.799559 |

Average percentage repellency of female Aedes aegypti to the tested compounds in a 1-choice trap assay.
One heat source at 37 C. is used as attractant.

REFERENCES

The following publications are incorporated by reference herein in their entirety:

Bohbot, J. D., and Dickens, J. C. (2012). Odorant receptor modulation: ternary paradigm for mode of action of insect repellents. Neuropharmacology 62, 2086-2095.

Boyle, S. M., McInally, S., and Ray, A. (2013). Expanding the olfactory code by in silico decoding of odor-receptor chemical space. Elife 2, e01120.

Corbel, V., Stankiewicz, M., Pennetier, C., Fournier, D., Stojan, J., Girard, E., Dimitrov, M., Molgo, J., Hougard, J. M., and Lapied, B. (2009). Evidence for inhibition of cholinesterases in insect and mammalian nervous systems by the insect repellent deet. Bmc Biol 7, -.

Ditzen, M., Pellegrino, M., and Vosshall, L. B. (2008). Insect odorant receptors are molecular targets of the insect repellent DEET. Science 319, 1838-1842.

Gupta, R. K. a. B., A. K. (2007). Discovery and Design of New Arthropod/Insect Repellents by Computer-Aided Molecular Modeling. In Insect Repellents: principles, methods, and uses, M. Debboun, Frances, S. P., Strickman, D., ed. (Boca Raton: Taylor & Francis Group), pp. 195-228.

Kain, P., Boyle, S. M., Tharadra, S. K., Guda, T., Pham, C., Dahanukar, A., and Ray, A. (2013). Odour receptors and neurons for DEET and new insect repellents. Nature 502, 507-512.

Klun, J. A., Strickman, D., Rowton, E., Williams, J., Kramer, M., Roberts, D., and Debboun, M. (2004). Comparative resistance of Anopheles albimanus and Aedes aegypti to N,N-diethyl-3-methylbenzamide (Deet) and 2-methylpiperidinyl-3-cyclohexen-1-carboxamide (AI3-37220) in laboratory human-volunteer repellent assays. J Med Entomol 41, 418-422.

Krajick, K. (2006). Medical entomology—Keeping the bugs at bay. Science 313, 36-38.

Liu, C., Pitts, R. J., Bohbot, J. D., Jones, P. L., Wang, G., and Zwiebel, L. J. (2010). Distinct olfactory signaling mechanisms in the malaria vector mosquito Anopheles gambiae. PLoS Biol 8.

Pellegrino, M., Steinbach, N., Stensmyr, M. C., Hansson, B. S., and Vosshall, L. B. (2011). A natural polymorphism alters odour and DEET sensitivity in an insect odorant receptor. Nature.

Reeder, N. L., Ganz, P. J., Carlson, J. R., and Saunders, C. W. (2001). Isolation of a DEET-insensitive mutant of Drosophila melanogaster (Diptera: Drosophilidae). J Econ Entomol 94, 1584-1588.

Stanczyk, N. M., Brookfield, J. F., Ignell, R., Logan, J. G., and Field, L. M. (2010). Behavioral insensitivity to DEET in *Aedes aegypti* is a genetically determined trait residing in changes in sensillum function. Proc Natl Acad Sci USA 107, 8575-8580.

Syed, Z., and Leal, W. S. (2008). Mosquitoes smell and avoid the insect repellent DEET. P Natl Acad Sci USA 105, 13598-13603.

Syed, Z., Pelletier, J., Flounders, E., Chitolina, R. F., and Leal, W. S. (2011). Generic insect repellent detector from the fruit fly *Drosophila melanogaster*. PLoS ONE 6, e17705.

Tauxe, G. M., MacWilliam, D., Boyle, S. M., Guda, T., and Ray, A. (2013). Targeting a dual detector of skin and CO2 to modify mosquito host seeking. Cell 155, 1365-1379.

Xia, Y., Wang, G., Buscariollo, D., Pitts, R. J., Wenger, H., and Zwiebel, L. J. (2008). The molecular and cellular basis of olfactory-driven behavior in *Anopheles gambiae* larvae. Proc Natl Acad Sci USA 105, 6433-6438.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method of repelling an arthropod, comprising: exposing the arthropod to a composition in an amount effective to repel the arthropod,
    wherein the composition comprises:
        (i) a carrier; and
        (ii) one or more of 6-methoxyquinoline, 4-amino-5-(3-(isopropyl amino)-2,2-dimethyl-3-oxopropoxy)-2-methyl quinoline-3-carboxylic acid, and 1,2,3,4-tetrahydroquinoline, or any pharmaceutically acceptable or environmentally acceptable salt thereof.

2. The method of claim 1, wherein the arthropod is exposed to the composition by applying the composition to: a subject; an article worn or associated with a subject; an agricultural product; a storage container, shipping container or transport container for an agricultural product; a structure or part of a structure from which the arthropod is to be repelled; or an area from which the arthropod is to be repelled.

3. The method of claim 2, wherein the subject is an animal or a plant.

4. The method of claim 3, wherein the subject is a human.

5. The method of claim 1, wherein the arthropod is an insect, tick, mite, spider, centipede, or scorpion.

6. The method of claim 1, wherein the arthropod is a household or agricultural pest.

7. The method of claim 1, wherein the arthropod is a blood-feeding arthropod.

8. The method of claim 7, wherein the blood-feeding arthropod is a mosquito, gadfly, louse, bedbug, sandfly, black fly, tsetse fly, midge, mite, or flea.

9. A method of repelling an arthropod, comprising: exposing the arthropod to a composition in an amount effective to repel the arthropod,
    wherein the composition comprises:
        (i) a carrier; and
        (ii) one or more of isobutyl quinolone, 6-methyl quinolone, and isopropyl quinolone, or any pharmaceutically acceptable or environmentally acceptable salt thereof.

10. The method of claim 9, wherein the arthropod is exposed to the composition by applying the composition to: a subject; an article worn or associated with a subject; an agricultural product; a storage container, shipping container or transport container for an agricultural product; a structure or part of a structure from which the arthropod is to be repelled; or an area from which the arthropod is to be repelled.

11. The method of claim 10, wherein the subject is an animal or a plant.

12. The method of claim 11, wherein the subject is a human.

13. The method of claim 9, wherein the arthropod is an insect, tick, mite, spider, centipede, or scorpion.

14. The method of claim 9, wherein the arthropod is a household or agricultural pest.

15. The method of claim 9, wherein the arthropod is a blood-feeding arthropod.

16. The method of claim 15, wherein the blood-feeding arthropod is a mosquito, gadfly, louse, bedbug, sandfly, black fly, tsetse fly, midge, mite, or flea.

* * * * *